US007632935B2

(12) United States Patent
Kitamura et al.

(10) Patent No.: US 7,632,935 B2
(45) Date of Patent: Dec. 15, 2009

(54) DNA ENCODING A MAST CELL-DERIVED MEMBRANE PROTEIN

(75) Inventors: Toshio Kitamura, 6-16-20-406, Shirokane, Minato-ku, Tokyo 108-0072 (JP); Hidetoshi Kumagai, Coppell, TX (US)

(73) Assignees: Chungai Seiyaku Kabushiki Kaisha, Tokyo (JP); Toshio Kitamura, Tokyo (JP)

( * ) Notice: Subject to any disclaimer, the term of this patent is extended or adjusted under 35 U.S.C. 154(b) by 442 days.

(21) Appl. No.: 10/531,973

(22) PCT Filed: Oct. 30, 2003

(86) PCT No.: PCT/JP03/13921

§ 371 (c)(1),
(2), (4) Date: Nov. 18, 2005

(87) PCT Pub. No.: WO2004/039981

PCT Pub. Date: May 13, 2004

(65) Prior Publication Data

US 2006/0121484 A1    Jun. 8, 2006

(30) Foreign Application Priority Data

Oct. 30, 2002  (JP)  ............................. 2002-316680
Dec. 5, 2002   (JP)  ............................. 2002-354165

(51) Int. Cl.
*C07H 21/04* (2006.01)
*C12N 15/00* (2006.01)
*C12N 5/10* (2006.01)
*C12P 21/02* (2006.01)

(52) U.S. Cl. .................. 536/23.5; 536/23.1; 536/24.31; 536/24.33; 435/320.1; 435/252.3; 435/455; 435/69.1

(58) Field of Classification Search ........................ None
See application file for complete search history.

(56) References Cited

FOREIGN PATENT DOCUMENTS

| JP | 2002-316680 | * | 10/2002 |
|----|-------------|---|---------|
| JP | 2002-354165 | * | 12/2002 |
| WO | WO 01/66720 A1 | | 9/2001 |

OTHER PUBLICATIONS

GenBank entry of Accession No. AK045869 (1999).*
Attwood T., Science 2000; 290:471-473.*
Skolnick et al., Trends in Biotech. 2000; 18(1):34-39.*
Metzler et al., Nature Structural Biol. 1997; 4:527-531.*
Genbank Accession No. AK045869, revision history (provided by Applicant).*
Carninci and Hayashizaki, Meth. Enzymol. 303:19-44, 1999 (provided by Applicant).*
Carninci et al., Genome Res. 10:1617-30, 2000 (provided by Applicant).*
Shibata et al., Genome Res. 10:1757-71, 2000 (provided by Applicant).*
Kawai et al., Nature 409:685-690, 2001 (provided by Applicant).*
Billadeau, D.D. et al., "ITAMs versus ITIMs: striking a balance during cell regulation", J. Clin. Invest., 109(2):161-8 (2002).
Clark, G.J. et al., "The CMRF-35H gene structure predicts for an independently expressed member of an ITIM/ITAM pair of molecules localized to human chromosome 17", Tissue Antigens, 55(2):101-9 (2000).
Clark, G.J. et al., "The gene encoding the immunoregulatory signaling molecule CMRF-35A localized to human chromosome 17 in close proximity to other members of the CMRF-35 family", Tissue Antigens, 57(5):415-23 (2001).
Kumagai, H. et al., "Identification and characterization of a new pair of immunoglobulin-like receptors LMIR1 and 2 derived from murine bone marrow-derived mast cells", Biochem. Biophys. Res. Commun., 307(3):719-29 (2003).
Lanier, L.L. et al., "The ITAM-bearing transmembrane adaptor DAP12 in lymphoid and myeloid cell function", Immunol. Today, 21(12):611-4 (2000).
Luo, K. et al., "DIgR1, a novel membrane receptor of the immunoglobulin gene superfamily, is preferentially expressed by antigen-presenting cells", Biochem. Biophys. Res. Commun., 287(1):35-41 (2001).
Malbec, O. et al., "Fc receptor I-associated lyn-dependent phosphorylation of Fc receptor IIB during negative regulation of mast cell activation", J. Immunol., 160(4):1647-58 (1998).
Mu, X. et al., "Gene expression in the developing mouse retina by EST sequencing and microarray analysis", Nucleic Acids Res., 29(24):4983-93 (2001).
Samuelsson, A. et al., "Anti-inflammatory activity of IVIG mediated through the inhibitory Fc Receptor", Science, 291(5503):484-6 (2001).
Smith, K.G., et al., "Inhibition of the B cell by CD22: A requirement for Lyn", J. Exp. Med., 187(5):807-11 (1998).
Tomasello, E. et al., "Association of signal-regulatory proteins with KARAP/DAP-12", Eur. J. Immunol., 30(8):2147-56 (2000).
Vely, F. et al., "Commentary: Conservation of structural features reveals the existence of a large family of inhibitory cell surface receptors and noninhibitory/activatory counterparts", J. Immunol., 159(5):2075-7 (1997).
Wu, J. et al., "DAP10 and DAP12 Form Distinct, but Functionally Cooperative, Receptor Complexes in Natural Killer Cells", J. Exp. Med., 192(7):1059-68 (2000).

(Continued)

*Primary Examiner*—Ilia Ouspenski
(74) *Attorney, Agent, or Firm*—Fish & Richardson P.C.

(57) ABSTRACT

An originally developed efficient signal sequence trapping method was used to screen a cDNA library prepared from cultured mast cells derived from mouse bone marrow. As a result, genes encoding type I membrane proteins and comprising a single immunoglobulin domain in the extracellular domain and a motif for transmitting an inhibitory signal into cells were successfully isolated.

17 Claims, 9 Drawing Sheets

OTHER PUBLICATIONS

Yotsumoto, K. et al., "Paired activating and inhibitory immunoglobulin-like receptors, MAIR-1 and MAIR-II, regulate mast cell and macrophage activation", J. Exp. Med., 198(2):223-33 (2003).

GenBank Accession No. BG803833, "0242-40 Mouse E14.5 retina lambda ZAP II Library Mus musculus cDNA, mRNA sequence" (2001).

EMBL Accession No. AF251704, "Mus musculus polymeric immunoglobulin receptor 4 precursor (Pigr4) mRNA, complete cds." (2002).

EMBL Accession No. AL669969, "Mouse DNA sequence from clone RP23-254J18 on chromosome 11" (2002).

* cited by examiner

FIG. 1

```
   1 ACAGAACTGAGGAAAGTCAGAAGCAAAACAGCTAGACACAAAGAAAAGCAGAAGTGGGCTGTCTCAGAGACTGGCCGTCCCCTAGCGGGA
  91 CTGAACCGTGGAGCGTCCAGCCGTGGCCTGCCTGCCGGTGACCCGTGTGTGGGAGAAATGACCCAACTGGCCTCAGCTGTGTGGCTGCCC
   1                                                             m  t  q  l  a  s  a  v  w  l  p
 181 ACGCTGTTGCTGCTGCTGCTGCTTTTTTTGGCTTCCAGGCTGTGTCCCTCTGCATGGTCCCAGCACCATGACAGGAAGTGTGGGTCAATCC
  12  t  l  l  l  l  l  l  f  w  l  p  g  c  v  p  L  H  G  P  S  T  M  T  G  S  V  G  Q  S
 271 CTGAGTGTGTCGTGTCAGTATGAGGAGAAATTTAAGACTAAGGACAAATACTGGTGCAGAGGGTCACTTAAGGTACTGTGCAAAGATATT
  42  L  S  V  S  C  Q  Y  E  E  K  F  K  T  K  D  K  Y  W  C  R  G  S  L  K  V  L  C  K  D  I
 361 GTCAAGACCAGCAGCTCAGAAGAAGCTAGGAGTGGCAGAGTGACCATCAGGGACCATCCAGACAACCTCACCTTCACAGTGACCTATGAG
  72  V  K  T  S  S  E  E  A  R  S  G  R  V  T  I  R  D  H  P  D  N  L  T  F  T  V  T  Y  E
 451 AGCCTCACCCTGGATGATGCAGACACCTACATGTGTGCCGTGGATATACCATTTTTCAATGCCCCCTTGGGGCTCGATAAGTACTTCAAG
 102  S  L  T  L  D  D  A  D  T  Y  M  C  A  V  D  I  P  F  F  N  A  P  L  G  L  D  K  Y  F  K
 541 ATTGAATTGTCTGTGGTTCCAAGTGAGGACCCAGTTTCATCTCCAGGACCAACACTAGAGACACCTGTGGTGTCCACCAGTCTGCCTACC
 132  I  E  L  S  V  V  P  S  E  D  P  V  S  S  P  G  P  T  L  E  T  P  V  V  S  T  S  L  P  T
 631 AAGGGTCCCGCCCTAGGATCCAACACAGAGGACCGCCGTGAGCATGACTATTCCCAGGGCTTGAGGCTCCCAGCGCTGTTGTCTGTGTTA
 162  K  G  P  A  L  G  S  N  T  E  D  R  R  E  H  D  Y  S  Q  G  L  R  L  P  A  L  L  S  V  L
 721 GCTCTCCTGCTGTTTCTGTTGGTGGGGACATCTCTGCTGGCCTGGAGGATGTTCCAGAAGCGGCTGGTCAAAGCTGATAGGCATCCAGAG
 192  A  L  L  L  F  L  L  V  G  T  S  L  L  A  W  R  M  F  Q  K  R  L  V  K  A  D  R  H  P  E
 811 CTGTCCCAGAACCTCAGACAGGCTTCTGAGCAGAATGAGTGCCAGTATGTGAATTTGCAGCTGCACACGTGGTCTCTGAGGGAAGAGCCG
 222  L  S  Q  N  L  R  Q  A  S  E  Q  N  E  C  Q  Y  V  N  L  Q  L  H  T  W  S  L  R  E  E  P
 901 GTGCTACCAAGTCAGGTAGAAGTGGTGGAATATAGCACATTGGCATTACCCCAGGAAGAGCTTCACTATTCATCCGTGGCATTCAACTCC
 252  V  L  P  S  Q  V  E  V  V  E  Y  S  T  L  A  L  P  Q  E  E  L  H  Y  S  S  V  A  F  N  S
 991 CAGAGGCAGGATTCTCACGCCAATGGAGATTCTCTTCATCAACCTCAGGACCAGAAAGCAGAGTACAGTGAGATCCAGAAGCCCAGAAAA
 282  Q  R  Q  D  S  H  A  N  G  D  S  L  H  Q  P  Q  D  Q  K  A  E  Y  S  E  I  Q  K  P  R  K
1081 GGACTCTCTGACCTTTACCTGTGACTCCTTGTCACCTGATCCTCTCAGTGGTGACTACCAGGTTCCAAGGCTCCCTGCTGGCTGCTGCCC
 312  G  L  S  D  L  Y  L  *
1171 TCAATGTCATGAGCCTCAGTGGCTTCACTAAAGATGAGCAGGAGCCAGGGCTCTGTGGGCACAGTCTCATCCCACTGGCTCTCTCCTCTT
1261 AGCCTGTATTTTGTTCTGCCTCTGGGTGTGGAAGACATCGATGCTGCTCTTTTGGGGCTCTGGGAATTGACATGGTTCGTATAGAACGGT
1351 ACTTGTGTTAGTTAGCTTTGTAGTGTCAGTCCAGGAAGAACATCTGTGGTCACTGGGAAAGTGGGGGACCCATGAGACTACAAAGGAAGG
1440 GGAGTCATGGAGGTACTAAACACCAACTCCTTCATCTCACAGAGAAAAAAACCTAAGCTCTGAGGACAAAAGCCTGGCCCGTGGCACCAA
1531 GGTCAGGGGCAAATTCCTCTGGACTCATTTTTATTTTTATTTTTTGTTTTTTGAGACAGGGTCTCTCTGTGTAGCTTTGGCTGTCCTGGA
1621 ACTCACTCTGTAAACCAGAATGGCCTCAGACTCACAAAGATCTGCCTGCCTCTGCCTCCAAAGGTGTGTGCCACAATGCCTGGCTTCTCT
1711 GAATTCTTAAGTAAAAGATGAAATAAAGTTTATAATATCTTT
```

FIG. 2

```
  1  ATGATTCCCAGAGTAATAAGATTGTGGCTGCCTTCAGCTCTGTTCCTCTCTCAGGTCCCAGGCTGTGTCCCACTGCATGGCCCCAGCACT
  1    m  i  p  r  v  i  r  l  w  l  p  s  a  l  f  l  s  q  v  p  g  c  v  p  L  H  G  P  S  T
 91  ATCACAGGCGCTGTTGGGGAATCGCTCAGTGTGTCATGTCAATACGAGGAGAAATTCAAGACTAAGGACAAATTCTGGTGCAGAGGGTCA
 31    I  T  G  A  V  G  E  S  L  S  V  S  C  Q  Y  E  E  K  F  K  T  K  D  K  F  W  C  R  G  S
181  CTGAAGGTACTCTGTAAAGATATTGTCAAGACCAGCAGCTCAGAAGAAGTTAGGAATGGCCGAGTGACCATCAGGGACCATCCAGACAAC
 61    L  K  V  L  C  K  D  I  V  K  T  S  S  S  E  E  V  R  N  G  R  V  T  I  R  D  H  P  D  N
271  CTCACCTTCACAGTGACCTATGAGAGCCTCACCCTGGAGGATGCAGACACCTACATGTGTGCGGTGGATATATCACTTTTTGATGGCTCC
 91    L  T  F  T  V  T  Y  E  S  L  T  L  E  D  A  D  T  Y  M  C  A  V  D  I  S  L  F  D  G  S
361  TTGGGGTTCGATAAGTACTTCAAGATTGAGTTGTCTGTGGTTCCAAGTGAGGACCCAGTCACAGGTTCGAGCCTTGAGAGTGGTAGAGAT
121    L  G  F  D  K  Y  F  K  I  E  L  S  V  V  P  S  E  D  P  V  T  G  S  S  L  E  S  G  R  D
451  ATCCTGGAATCCCCCACATCCTCAGTTGGGCACACTCATCCCAGTGTGACCACAGATGACACAATTCCTGCTCCCTGCCCTCAGCCTCGG
151    I  L  E  S  P  T  S  S  V  G  H  T  H  P  S  V  T  T  D  D  T  I  P  A  P  C  P  Q  P  R
541  TCTCTTCGGAGCAGCCTCTACTTCTGGGTCCTGGTGTCTCTGAAGTTGTTCCTGTTCCTGAGCATGCTTGGTGCTGTCCTCTGGGTGAAC
181    S  L  R  S  S  L  Y  F  W  V  L  V  S  L  K  L  F  L  F  L  S  M  L  G  A  V  L  W  V  N
631  AGGCCTCAGAGGTGCTCTGGGGGAAGCAGCACTCAGCCCTGTTATGAGAACCAGTGA
211    R  P  Q  R  C  S  G  G  S  S  T  Q  P  C  Y  E  N  Q  *
```

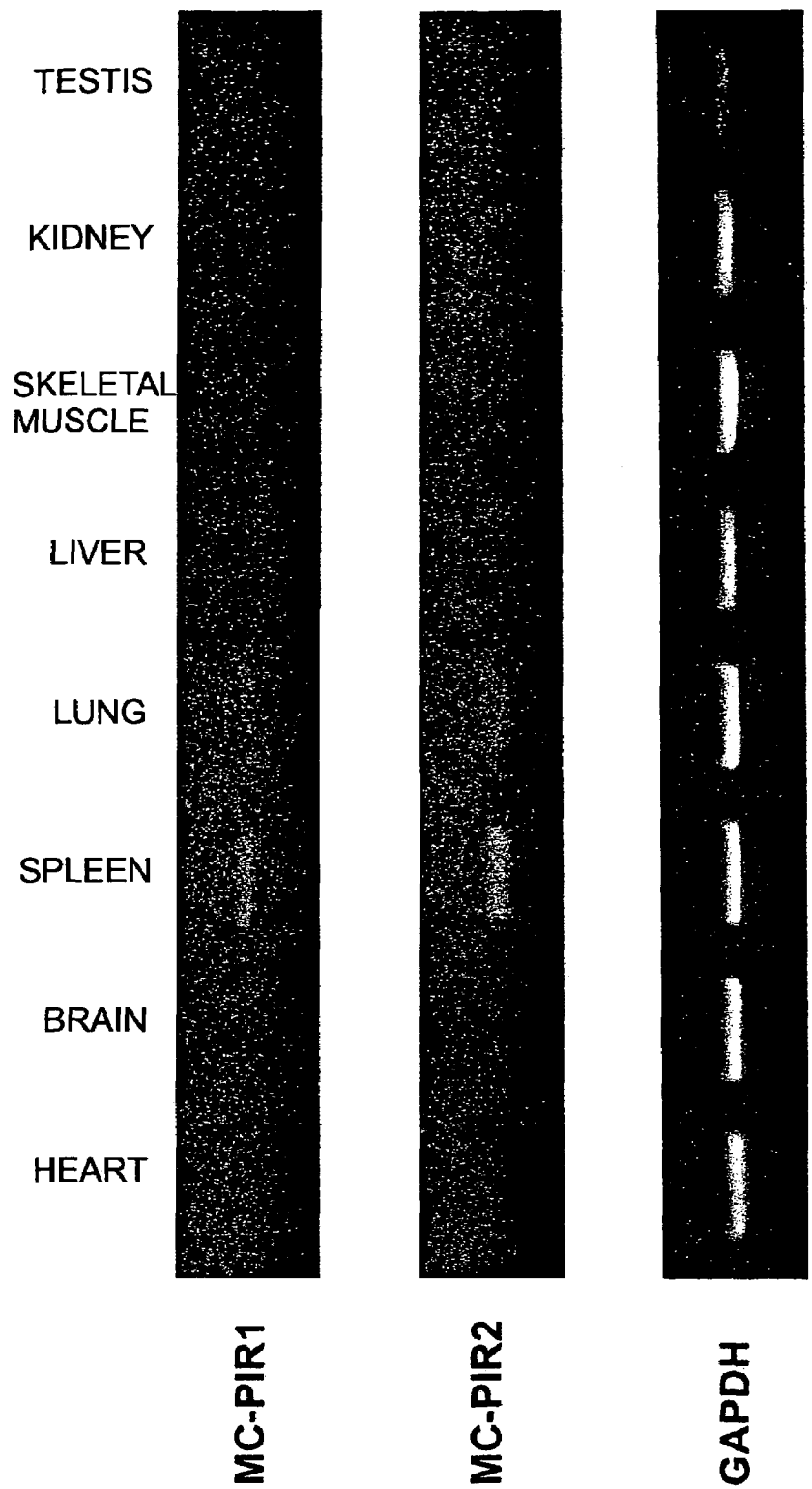

FIG. 7
| | Fcγ RIIb | | | Fc-PIR1 | | |
|---|---|---|---|---|---|---|
| α-MOUSE IgG, F(ab')₂ | - | + | - | - | + | - |
| α-MOUSE IgG, INTACT | - | - | + | - | - | + |
BLOT : α SHP-1
| | Fcγ RIIb | | | Fc-PIR1 | | |
|---|---|---|---|---|---|---|
| α-MOUSE IgG, F(ab')₂ | - | + | - | - | + | - |
| α-MOUSE IgG, INTACT | - | - | + | - | - | + |
BLOT : α SHP-2
| | Fcγ RIIb | | | Fc-PIR1 | | |
|---|---|---|---|---|---|---|
| α-MOUSE IgG, F(ab')₂ | - | + | - | - | + | - |
| α-MOUSE IgG, INTACT | - | - | + | - | - | + |
BLOT : α SHIP

IMMUNOPRECIPITATION : αHA

|  | MC-PIR2-HA | | | |
|---|---|---|---|---|
| MOCK | + | − | − | − |
| FLAG-DAP10 | − | + | − | − |
| FLAG-DAP12 | − | − | + | − |
| FLAG-FcRγ | − | − | − | + |

WESTERN BLOT : αFLAG

DNA ENCODING A MAST CELL-DERIVED MEMBRANE PROTEIN

CROSS-REFERENCE TO RELATED APPLICATIONS

This application is the National Stage of International Application No. PCT/JP2003/013921, filed Oct. 30, 2003, which claims the benefit of Japanese Patent Applications Serial No. 2002-316680, filed on Oct. 30, 2002, and 2002-354165, filed on Dec. 5, 2002. The contents of all applications are hereby incorporated by reference in their entireties.

TECHNICAL FIELD

The present invention relates to novel membrane proteins derived from mast cells and genes encoding them, as well as methods for producing them and uses thereof.

BACKGROUND ART

Mast cells are known to act as effector cells in allergic diseases such as atopic dermatitis, rhinitis, and asthma by releasing inflammation-associated substances such as histamine upon antigen stimulation. Antihistamines or steroids that suppress the production or release of inflammation-associated substances from mast cells, or drugs that antagonize the effect of such substances, are currently being used for the treatment of these allergic diseases. However, the development of effective drugs with higher selectivity is being anticipated.

Molecules such as FcγRIIB, gp49B, and SIRPα have been known as candidates of membrane proteins participating in the regulation of mast cell signal transduction. However, the whole picture of the mechanism that regulates responses to antigen stimulation associated with allergic diseases remains unclear.

DISCLOSURE OF THIS INVENTION

The present invention provides novel membrane proteins thought to play a role in the regulation of mast cell signal transduction, genes encoding them, as well as methods for producing them and uses thereof. The membrane proteins of this invention would be useful for elucidating the mechanisms that regulate responses to antigen stimulation, or transduction of survival or proliferation signals in mast cells.

In order to solve the above problems, the present inventors prepared a cDNA library from mouse bone marrow-derived cultured mast cells, a well characterized mast cell model. They then screened this library for molecules containing signal peptides (von Heijne J. Mol. Biol. 184: 99-105 (1985)) using an efficient signal sequence trapping system (the SST-REX method) (Kojima T. and Kitamura T. Nature Biotechnol. 17: 487-490 (1999)), which was developed by the inventors themselves using a retrovirus-mediated expression cloning system (Kitamura T. et al. Proc. Natl. Acad. Sci. USA 92: 9146-9150 (1995)). In the SST-REX method, a library expressing fusion proteins with the constitutively active form of cytokine receptor MPL is screened to look for a cDNA(s) encoding a protein(s) capable of inducing the cell surface expression of the MPL. As the index used in the method is the acquisition of autonomous proliferation capability in IL-3 dependent cell lines as a result of MPL expression on the cell surface, a clone of interest can be easily selected.

After screening $2.0 \times 10^6$ clones, a gene encoding a type I membrane protein and having a single immunoglobulin domain in the extracellular domain and a motif for transmitting an inhibitory signal into cells was identified. The protein was named MC-PIR1 (later renamed as LMIR1). In addition, a molecule whose amino acid sequence showed approximately 90% homology with the immunoglobulin domain of MC-PIR1 was isolated from the same library, and named MC-PIR2 (later renamed as LMIR2).

These genes had an expression profile specific to mast cells. Furthermore, MC-PIR1 was phosphorylated upon cross-linking, and was capable of binding to the phosphotyrosine phosphatases SHP-1 and SHP-2, and phosphoinositide phosphatase SHIP, which are adaptor proteins involved in the regulation of signal transduction. MC-PIR2 was found to form a complex with DAP10, DAP12, and FcRγ, ITAM-comprising signaling molecules. Therefore, these proteins are likely to be membrane proteins participating in the regulation of mast cell signal transduction.

MC-PIR1 and MC-PIR2 genes are derived from mouse. A DNA search using their nucleotide sequences identified human gene homologues CMRF-35H, Irp60, and CMRF-35A. Since these human genes were not known to participate in the regulation of mast cell signal transduction, the information obtained through MC-PIR1 and MC-PIR2 provides novel uses for the gene products of these human genes.

Natural ligands for MC-PIR1, MC-PIR2, and the human homologues thereof have not been identified, but the use of these gene products would facilitate the discovery of these natural ligands. Similarly, the gene products may also be useful in screenings for compounds that mimic the function of natural ligands, or antibodies. Such compounds or antibodies, obtained by the above screenings, have the potential to inhibit the transduction of the mast cell activation signal, and thus be anti-allergy drugs with a new mechanism of action.

The present invention relates to mast cell-derived membrane proteins, gene encoding them, and molecules functionally equivalent to these, as well as methods for producing them, and uses thereof. More specifically, the present invention provides:

(1) a DNA according to any one of the following (a) to (d):
   (a) a DNA encoding a protein comprising the amino acid sequence of SEQ ID NO: 2 or 4,
   (b) a DNA comprising the coding region of the nucleotide sequence of SEQ ID NO: 1 or 3,
   (c) a DNA encoding a protein comprising an amino acid sequence in which one or more amino acids in the amino acid sequence of SEQ ID NO: 2 or 4 have been replaced, deleted, inserted, and/or added,
   (d) a DNA capable of hybridizing with a DNA comprising the nucleotide sequence of SEQ ID NO: 1 or 3 under stringent conditions;
(2) the DNA of (1) encoding a protein capable of binding to a protein selected from the group consisting of SHP-1 protein, SHP-2 protein, SHIP protein, DAP10 protein, DAP12 protein, and FcRγ protein;
(3) a protein encoded by the DNA of (1);
(4) a vector into which the DNA of (1) has been inserted;
(5) a host cell carrying the DNA of (1), or the vector of (4);
(6) a method for producing the protein of (3), which comprises the steps of culturing the host cell of (5), and recovering an expressed protein from said host cell or the culture supernatant thereof;
(7) an antibody that binds to the protein of (3);
(8) a polynucleotide comprising at least 15 nucleotides that is complementary to a DNA comprising the nucleotide sequence of SEQ ID NO: 1 or 3, or the complementary strand thereof;

(9) a method of screening for a compound that binds to the protein of (3), which comprises the following steps of:
(a) contacting said protein with a test sample,
(b) detecting the binding activity between said protein and said test sample, and
(c) selecting a compound capable of binding to said protein;

(10) a method of screening for a compound capable of inhibiting the binding between the protein of (3) and a protein selected from the group consisting of SHP-1 protein, SHP-2 protein, SHIP protein, DAP10 protein, DAP12 protein, and FcRγ protein, which comprises the following steps of:
(a) contacting the protein of (3) with a protein selected from said group in the presence of a test sample,
(b) detecting the binding activity between said proteins, and
(c) selecting a compound capable of reducing the binding activity between said proteins compared to that detected in the absence of said test sample;

(11) a method for producing an anti-allergy drug, which comprises the step of mixing the antibody of (7), or a compound obtained using the method of (9) or (10), with a pharmacologically acceptable carrier or vehicle.

The present invention provides DNAs encoding novel membrane proteins derived from mast cells, which are thought to participate in the regulation of the signal transduction in mast cells.

Using a recently established novel signal sequence trapping method (the ST-REX method), the present inventors searched a cDNA library prepared from mouse bone marrow-derived cultured mast cells, and identified two genes, each of which encodes a type I membrane protein and comprises a single immunoglobulin domain in the extracellular domain and a motif for transmitting an inhibitory signal into cells. The nucleotide sequence of the gene named MC-PIR1 is shown in SEQ ID NO: 1. The amino acid sequence of a protein encoded by the gene is shown in SEQ ID NO: 2. In addition, the nucleotide sequence of the gene named MC-PIR2, having approximately 90% homology at the amino acid level with the immunoglobulin domain of MC-PIR1, is shown in SEQ ID NO: 3, and the amino acid sequence of a protein encoded by the gene is shown in SEQ ID NO: 4. These genes are expressed specifically in mast cells. In addition, MC-PIR1 is phosphorylated in response to antigen stimulation, and is capable of binding to phosphotyrosine phosphatases SHP-1 and SHP-2 and phosphoinositide phosphatase SHIP, which are adaptor proteins participating in the regulation of signal transduction. On the other hand, MC-PIR2 is capable of forming a complex with DAP10, DAP12, and FcRγ, which are signaling molecules comprising ITAM. Thus, these proteins of the present invention are considered to be membrane proteins participating in the regulation of mast cell signal transduction. Such proteins are expected to be useful, for example, for the development of anti-allergy drugs having a novel mechanism of action through inhibiting the transduction of the activation signal in mast cells.

In addition, the present invention comprises a protein functionally equivalent to a protein encoded by MC-PIR1 DNA or MC-PIR2 DNA (comprising the nucleotide sequence according to SEQ ID NO: 1 or 3). Such proteins include, for example, mutants of these proteins, their homologues in organisms other than mouse, and so on. Herein, the phrase "functionally equivalent" means that the protein of interest has a biological or biochemical activity similar to the MC-PIR1 and MC-PIR2 proteins. For example, such an activity may be the ability to undergo phosphorylation in response to antigen stimulation and bind to adaptor proteins involved in the regulation of signal transduction such as phosphotyrosine phosphatase SHP-1 and SHP-2 and phosphoinositide phosphatase SHIP, or the ability to bind to signaling molecules comprising ITAM such as DAP10, DAP12, and FcRγ.

To prepare a protein functionally equivalent to another protein, methods for introducing mutations into proteins are well known to those skilled in the art. For example, those skilled in the art can prepare a protein functionally equivalent to the MC-PIR1 or MC-PIR2 protein (comprising the amino acid sequence of SEQ ID NO: 2 or 4) by introducing an appropriate mutation into an amino acid(s) of the protein using site-directed mutagenesis (Hashimoto-Gotoh T. et al. Gene 152: 271-275(1995); Zoller M. J. and Smith M. Methods Enzymol. 100: 468-500(1983); Kramer W. et al. Nucleic Acids Res. 12: 9441-9456 (1984); Kramer W. and Fritz H. J. Methods Enzymol. 154: 350-367(1987); Kunkel T. A. Proc. Natl. Acad. Sci. USA 82: 488-492 (1985); Kunkel T. A. Methods Enzymol. 85: 2763-2766 (1988)). Amino acids mutations may also occur in nature. Thus, such a protein comprising an amino acid sequence in which one or more amino acids in the sequence of the MC-PIR1 or MC-PIR2 protein are mutated, and which is functionally equivalent to the MC-PIR1 or MC-PIR2 protein, is also included in the present invention. In such a mutant protein, the number of mutated amino acids is usually 50 or less, preferably 30 or less, and more preferably 10 or less (for example, five amino acids or less).

In mutating an amino acid, it is preferable to change it into another amino acid that allows the properties of the amino acid side chain to be conserved. Based on the properties of side chains, amino acids can be divided into, for example, the following groups: hydrophobic amino acids (A, I, L, M, F, P, W, Y, V), hydrophilic amino acids (R, D, N, C, E, Q, G, H, K, S, T), amino acids with an aliphatic side chain (G, A, V, L, I, P), amino acids with a side chain comprising a hydroxyl group (S, T, Y), amino acids with a side chain comprising sulfur (C, M), amino acids with a side chain comprising a carboxylic acid and an amide group (D, N, E, Q), basic amino acids (R, K, H), and aromatic amino acids (H, F, Y, W) (in the parentheses, amino acids are shown using the one letter code).

It is already known that a protein having a modified amino acid sequence, in which one or more amino acids are deleted, added, and/or substituted with another amino acid, can maintain the original biological activity (Mark D. F. et al. Proc. Natl. Acad. Sci. USA 81: 5662-5666 (1984); Zoller M. J. and Smith M. Nucleic Acids Res. 10: 6487-6500 (1982); Wang A. et al. Science 224: 1431-1433 (1984); Dalbadie-MeFarland G. et al. Proc. Natl. Acad. Sci. USA 79: 6409-6413 (1982)).

A protein comprising an amino acid sequence in which multiple amino acid residues are added to the sequence of MC-PIR1 or MC-PIR2 protein includes fusion proteins comprising these proteins. Fusion proteins such as those between the proteins of this invention and other peptides or proteins are included in the present invention. To produce a fusion protein, a DNA encoding the MC-PIR1 or MC-PIR2 protein (comprising the amino acid sequence according to SEQ ID NO: 2 or 4) and a DNA encoding another peptide or protein are ligated so that their frames match, and introduced into an expression vector to express in a host. Any method commonly known to those skilled in the art can be used. Any peptide or protein may be used for making a fusion protein with a protein of this invention.

Known peptides that can be used as peptides that are fused to the proteins of the present invention include, for example, FLAG (Hopp, T. P. et al., Biotechnology (1988) 6, 1204-1210), 6×His containing six histidine (HIS) residues, 10×His, HA (Influenza agglutinin), human c-myc fragment, VSP-GP fragment, p18HIV fragment, T7-tag, HSV-tag, E-tag, SV40T antigen fragment, lck tag, α-tubulin fragment, B-tag, Protein C fragment, and the like. Examples of proteins that may be fused to proteins of the invention include GST (glutathione-S-transferase), HA (Influenza agglutinin), immunoglobulin constant region, β-galactosidase, MBP (maltose-binding protein), and such.

Fusion proteins can be prepared by fusing commercially available DNA encoding the fusion peptides or proteins discussed above, with the DNA encoding the proteins of the present invention, and expressing the prepared fused DNA.

An alternative method known in the art to isolate functionally equivalent proteins is, for example, the method using hybridization (Sambrook, J. et al., Molecular Cloning 2nd ed. 9.47-9.58, Cold Spring Harbor Lab. Press, 1989). One skilled in the art can readily isolate a DNA having high homology with an entire or partial DNA sequence (SEQ ID NOs: 1 and 3) that encodes the MC-PIR1 and MC-PIR2 proteins, and isolate proteins functionally equivalent to the MC-PIR1 or MC-PIR2 protein using the isolated DNA.

The present invention includes proteins encoded by DNA that hybridize with DNA encoding the MC-PIR1 or MC-PIR2 protein, and which are functionally equivalent to the MC-PIR1 or MC-PIR2 protein. Such proteins include, for example, homologues in mice or other mammals (for example, a protein encoded by a human, rat, rabbit, or bovine homologous gene).

The conditions for hybridization used for isolating a DNA encoding a protein functionally equivalent to the MC-PIR1 or MC-PIR2 protein can be appropriately selected by those skilled in the art. For example, low stringent conditions may be used for hybridization. Low stringent conditions are post-hybridization washing in 0.1×SSC, 0.1% SDS at 42° C., for example, and preferably in 0.1×SSC, 0.1% SDS at 50° C. Highly stringent conditions are more preferable, which are washing in 5×SSC, 0.1% SDS at 65° C., for example. Under these conditions, a DNA having a higher homology can be efficiently obtained by increasing the temperature. Multiple factors including the temperature, salt concentration, and such are considered to affect the stringency of hybridization; one skilled in the art can achieve similar stringencies by appropriately selecting these factors.

In addition to hybridization, a gene amplification method such as the polymerase chain reaction (PCR) may be used for gene isolation using synthesized primers based on the nucleotide sequence of the DNA encoding the MC-PIR1 or MC-PIR2 protein (SEQ ID NO: 1 or 3).

Normally, such a protein encoded by the DNA isolated using the above hybridization techniques or gene amplification, and which is functionally equivalent to the MC-PIR1 or MC-PIR2 protein, has a high homology with these proteins (comprising the amino acid sequence of SEQ ID NO: 2 or 4) at the amino acid level. The proteins of this invention include proteins functionally equivalent to the MC-PIR1 or MC-PIR2 protein, and having a high homology with these proteins at the amino acid level. High homology normally means an identity of at least 50% or more at the amino acid level, preferably 75% or more, more preferably 85% or more, and most preferably 95% or more (96% or more, 97% or more, 98% or more, or 99% or more). Homology between proteins can be determined according to the algorithm described in literature (Wilbur W. J. and Lipman D. J. Proc. Natl. Acad. Sci. USA 80: 726-730 (1983)).

The proteins of the present invention may have variations in the amino acid sequence, molecular weight, isoelectric point, or presence or composition of sugar chains, depending on the cell or host used for producing it, or the method of purification, as described later on. Nevertheless, such proteins are included in the present invention as long as they are functionally equivalent to the MC-PIR1 or MC-PIR2 protein. For example, if a protein of the present invention is expressed in a prokaryotic cell such as $E.\ coli$, a methionine may be attached to the N-terminus of the original protein. Such proteins are also included in the present invention.

The proteins of the present invention can be prepared as recombinant proteins or natural proteins, by methods well known to those skilled in the art. A recombinant protein can be prepared by: inserting a DNA that encodes a protein of the present invention (for example, the DNA comprising the nucleotide sequence of SEQ ID NO: 1 or 3), into an appropriate expression vector; introducing the vector into an appropriate host cell; collecting thus obtained recombinants; obtaining an extract thereof; and purifying the protein by subjecting the extract to a chromatography. Examples of chromatographies are ion exchange chromatography, reverse phase chromatography, gel filtration, or affinity chromatography utilizing a column to which an antibody against a protein of the present invention is immobilized, or combinations of more than one of the aforementioned columns.

When the protein of the present invention is expressed within host cells (for example, animal cells or $E.\ coli$) as a fusion protein with the glutathione-S-transferase protein, or as a recombinant protein supplemented with multiple histidines, the expressed recombinant protein can be purified using a glutathione column or nickel column. After purifying the fusion protein, it is also possible to exclude regions other than the objective protein by cutting with thrombin or factor-Xa as required.

A natural protein may be isolated by a method known to those skilled in the art, for example, through purification by applying a tissue or cell extract expressing a protein of this invention onto an affinity column in which an antibody (described below) capable of binding to the protein has been immobilized. Both monoclonal and polyclonal antibodies can be used.

In addition, the present invention comprises partial peptides of the proteins of this invention. A partial peptide of this invention comprises an amino acid sequence of at least seven residues or more, preferably eight residues or more, and more preferably nine residues or more. The partial peptides may be useful, for example, for preparing antibodies against the proteins of this invention, in screenings for compounds capable of binding to the proteins, and in screenings for activators or inhibitors of the proteins. In addition, the peptides may be useful by themselves as antagonists or competitors of the proteins of this invention. The partial peptides of this invention can be produced using genetic engineering, by commonly known peptide synthesis methods, or digesting a protein of this invention with an appropriate peptidase. Peptide synthesis may be performed, for example, by either solid phase synthesis or liquid phase synthesis.

A DNA encoding a protein of the present invention would be useful not only for producing the protein in vivo or in vitro as described above, but also for applications in gene therapy of a disease caused by an abnormal function of the gene encoding the protein or a disease that can be treated with the protein, DNA diagnostics, etc. A DNA of this invention can take any form as long as it encodes a protein of this invention. It can be a cDNA synthesized from mRNA, genomic DNA, or chemically-synthesized DNA. In addition, it includes a DNA comprising any nucleotide sequence based on the degeneracy of genetic code as long as it encodes a protein of this invention.

A DNA of this invention can be prepared by methods commonly known to those skilled in the art. For example, it may be prepared by making a cDNA library from cells expressing a protein of this invention, and performing hybridization using a partial nucleotide sequence of the DNA (for example, SEQ ID NO: 1 or 3) as a probe. The cDNA library may be prepared, for example, according to the method described in literature (Sambrook J. et al. Molecular Cloning, Cold Spring Harbor Laboratory Press (1989)), or obtained from a commercial source. Alternatively, the DNA of this invention may be prepared as follows: RNA is prepared from cells expressing a protein of this invention, from which cDNA is synthesized using reverse transcriptase. Then, oligo DNA is synthesized based on the sequence of the DNA (for example, SEQ ID NO: 1 or 3), and used as a primer in a PCR reaction to amplify a cDNA encoding a protein of this invention.

Furthermore, the coding region of the cDNA can be determined by determining the nucleotide sequence of the obtained cDNA, and the amino acid sequence of a protein of this invention can be thus obtained. In addition, the obtained cDNA may be used as a probe for screening a genomic DNA library to isolate a genomic DNA.

Specific procedures are as follows: First, mRNA is isolated from a cell, tissue, or organ expressing a protein of this invention (for example, mast cells or tissues in which expression was detected by RT-PCR in the Example below). mRNA may be isolated by preparing total RNA using a commonly known method such as guanidine ultracentrifugation (Chirgwin J. M. et al. Biochemistry 18: 5294-5299 (1979)), or AGPC method (Chomczynski P. and Sacchi N. Anal. Biochem. 162: 156-159 (1987)), and then purifying mRNA from total RNA using an mRNA Purification Kit (Pharmacia), etc. Alternatively, mRNA may be directly prepared using the QuickPrep mRNA Purification Kit (Pharmacia).

The obtained mRNA is used to synthesize cDNA using reverse transcriptase. cDNA may be synthesized by using a commercially available kit such as the AMV Reverse Transcriptase First-strand cDNA Synthesis Kit (Seikagaku Kogyo). Alternatively, using a primer described herein, or such, cDNA may be synthesized and amplified following the 5'-RACE method (Frohman M. A. et al. Proc. Natl. Acad. Sci. U.S.A. 85:8998-9002 (1988); Belyavsky A. et al. Nucleic Acids Res. 17:2919-2932 (1989)) using the 5'-Ampli FINDER RACE Kit (Clontech) and the polymerase chain reaction (PCR).

A desired DNA fragment is prepared from PCR products and ligated with a vector DNA to produce a recombinant vector construct. This construct is used to transform *E. coli* or such, and desired recombinant vectors are prepared from a selected colony/colonies. The nucleotide sequence of the desired DNA can be verified by conventional methods such as dideoxynucleotide chain termination.

The nucleotide sequence of a DNA of the invention may be designed to be expressed more efficiently by taking into account the frequency of codon usage in the host used for the expression (Grantham R. et al. Nucleic Acids Res. 9:43-74 (1981)). The DNA of the present invention may be altered by a commercially available kit or a conventional method. For instance, the DNA may be altered by digestion with restriction enzymes, insertion of a synthetic oligonucleotide or an appropriate DNA fragment, addition of a linker, or insertion of an initiation codon (ATG) and/or a stop codon (TAA, TGA, or TAG).

The DNA of this invention specifically includes a DNA comprising the nucleotide sequence starting from "a" at 148 through "g" at 1101 in the nucleotide sequence of SEQ ID NO: 1, or a DNA comprising the nucleotide sequence from "a" at 1 through "g" at 684 in the sequence of SEQ ID NO: 3.

In addition, the DNA of this invention includes a DNA that hybridizes with a DNA comprising the nucleotide sequence shown as SEQ ID NO: 1 or 3 and encodes a protein functionally equivalent to an above-described protein of this invention. Hybridization conditions may be appropriately chosen by one skilled in the art. Specifically, the above-described specific conditions may be used. Under these conditions, the higher the temperature, the higher the homology of the obtained DNA would be. The above hybridizing DNA is preferably a naturally-occurring DNA, for example, a cDNA or chromosomal DNA.

The present invention also provides a vector into which a DNA of the present invention has been inserted. A vector of the present invention is useful to maintain a DNA of the present invention in a host cell, or to express a protein of the present invention.

When *E. coli* is a host cell and the vector is amplified and produced in a large amount in *E. coli* (e.g., JM109, DH5α, HB101, or XL1Blue), the vector should have "ori" to be amplified in *E. coli* and a marker gene for selecting transformed *E. coli* (e.g., a drug-resistance gene selected by a drug such as ampicillin, tetracycline, kanamycin, chloramphenicol, or the like). For example, M13-series vectors, pUC-series vectors, pBR322, pBluescript, pCR-Script, etc. can be used. In addition, pGEM-T, pDIRECT, and pT7 can also be used for subcloning and extracting cDNA as well as the vectors described above. When a vector is used to produce a protein of the present invention, an expression vector is especially useful. For example, an expression vector to be expressed in *E. coli* should have the above characteristics to be amplified in *E. coli*. When *E coli* such as JM109, DH5α, HB101, or XL1 Blue are used as a host cell, the vector should have a promoter, for example, the lacZ promoter (Ward et al., Nature (1989) 341, 544-546; FASEB J (1992) 6, 2422-2427), araB promoter (Better et al., Science (1988) 240, 1041-1043), or T7 promoter or the like, that can efficiently express the desired gene in *E. coli*. In this respect, pGEX-5X-1 (Pharmacia), "QIAexpress system" (Qiagen), pEGFP and pET (in this case, the host is preferably BL21 which expresses T7 RNA polymerase), for example, can be used in addition to the above vectors.

Additionally, the vector may also contain a signal sequence for polypeptide secretion. An example of a signal sequence that directs the protein to be secreted to the periplasm of the *E. coli* is the pelB signal sequence (Lei, S. P. et al J. Bacteriol. (1987) 169, 4379). Means for introducing the vectors into target host cells include, for example, the calcium chloride method and the electroporation method.

In addition to *E. coli*, for example, expression vectors derived from mammals (for example, pcDNA3 (Invitrogen) and pEGF-BOS (Nucleic Acids. Res. 1990, 18 (17), p5322), pEF, pCDM8), expression vectors derived from insect cells (for example, "Bac-to-BAC baculovirus expression system" (GIBCO BRL), pBacPAK8), expression vectors derived from plants (for example pMH1, pMH2), expression vectors derived from animal viruses (for example, pHSV, pMV, pAdexLcw), expression vectors derived from retroviruses (for example, pZIPneo), expression vector derived from yeast (for example, "*Pichia* Expression Kit" (Invitrogen), pNV11, SP-Q01), and expression vectors derived from *Bacillus subtilis* (for example, pPL608, pKTH50) can be used as vectors for producing a protein of the present invention.

In order to express the vector in animal cells such as CHO, COS, or NIH3T3 cells, the vector should have a promoter necessary for expression in such cells, for example, the SV40 promoter (Mulligan et al., Nature (1979) 277, 108), the MMLV-LTR promoter, the EF1α promoter (Mizushima et al., Nucleic Acids Res. (1990) 18, 5322), the CMV promoter, and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV, and pOP13.

In addition, when the aim is to stably express a gene and at the same time increase the copy number of the gene in cells, one can use the method of introducing, into CHO cells in which the nucleic acid synthesizing pathway is deleted, a vector comprising the complementary DHFR gene (for example pCHO I) and then amplifying this by methotrexate (MTX). Furthermore, when the aim is to transiently express a gene, one can use the method of transfecting a vector comprising a replication origin of SV40 (pcD, etc.) into COS cells comprising the SV40 T antigen expressing gene on the chromosome. The replication origin may also be derived from the polyoma virus, adenovirus, bovine papilloma virus (BPV), and the like. Furthermore, the expression vector may carry, as a selection marker, the aminoglycoside transferase (APH) gene, thymidine kinase (TK) gene, E. coli xanthine-guanine-phosphoribosyl transferase (Ecogpt) gene, dihydrofolate reductase (dhfr) gene, and such, for increasing the copy number in the host cell system.

A DNA of the present invention can further be expressed in vivo in animals, for example, by inserting the DNA into an appropriate vector and introducing it into living bodies by methods such as the retrovirus method, the liposome method, the cationic liposome method, and the adenovirus method. Gene therapy against diseases attributed to mutation of a gene encoding a protein of the present invention can be thus accomplished. An adenovirus vector (for example pAdexlcw) or retrovirus vector (for example, pZIPneo) can be given as an example of a vector, but the vector is not restricted thereto. General gene manipulations, such as insertion of a DNA of the present invention to a vector, can be performed according to conventional methods (Molecular Cloning, 5.61-5.63). Administration into a living body can be either an ex vivo method, or in vivo method.

The present invention further provides a host cell into which a vector of the present invention has been transfected. The host cell into which a vector of the invention is transfected is not particularly limited. For example, E. coli, various animal cells and such can be used. The host cells of the present invention can be used, for example, as a production system for producing or expressing a protein of the present invention. The present invention provides methods of producing a protein of the invention both in vitro and in vivo. For in vitro production, eukaryotic cells or prokaryotic cells can be used as host cells.

Useful eukaryotic cells may be animal, plant, or fungi cells. Animal cells include, for example, mammalian cells such as CHO (J. Exp. Med. 108:945 (1995)), COS, 3T3, myeloma, baby hamster kidney (BHK), HeLa, or Vero cells; amphibian cells such as Xenopus oocytes (Valle et al. Nature 291:340-358 (1981)); or insect cells such as Sf9, Sf21, or Tn5 cells. CHO cells lacking the DHFR gene (dhfr-CHO) (Proc. Natl. Acad. Sci. U.S.A. 77:4216-4220 (1980)) or CHO K-1 (Proc. Natl. Acad. Sci. U.S.A. 60:1275 (1968)) may also be used. Of animal cells, CHO cells are particularly preferable for mass expression. A vector can be transfected into host cells by, for example, the calcium phosphate method, the DEAE-dextran method, the cationic liposome DOTAP (Boehringer Mannheim), the electroporation method, the lipofection method, and so on.

As plant cells, plant cells derived from Nicotiana tabacum are known as protein-production systems, and may be used as callus cultures. As fungi cells, yeast cells such as Saccharomyces, including Saccharomyces cerevisiae, or filamentous fungi such as Aspergillus, including Aspergillus niger, are known and may be used herein.

Useful prokaryotic cells include bacterial cells such as E. coli, for example, JM109, DH5α, and HB101. Other bacterial systems include Bacillus subtilis.

These cells are transformed by a desired DNA, and the resulting transformants are cultured in vitro to obtain the protein. Transformants can be cultured using known methods. Culture medium for animal cells include, for example, DMEM, MEM, RPMI 1640, and IMDM. These may be used with or without a serum supplement such as the fetal calf serum (FCS). The pH of the culture medium is preferably between about 6 and 8. Such cells are typically cultured at about 30 to 40° C. for about 15 to 200 hr, and the culture medium may be replaced, aerated, or stirred if necessary.

Animal or plant hosts may be used for the in vivo production. For example, a desired DNA can be transfected into an animal or plant host. Encoded proteins are produced in vivo, and then recovered. These animal and plant hosts are included in the host cells of the present invention.

Animals used for the production system described above include, but are not limited to, mammals and insects. Mammals, such as goats, pigs, sheep, mice and cows, may be used (Vicki Glaser, SPECTRUM Biotechnology Applications (1993)). Alternatively, the mammals may be transgenic animals.

For instance, a desired DNA may be prepared as a fusion gene, by fusing it with a gene such as the goat β casein gene which encodes a protein specifically produced into milk. DNA fragments comprising the fusion gene are injected into goat embryos, which are then implanted in female goats. Proteins are recovered from milk produced by the transgenic goats (i.e., those born from the goats that had received the embryos) or from their offspring. To increase the amount of milk containing the proteins produced by the transgenic goats, appropriate hormones may be administered to them (Ebert K. M. et al. Bio/Technology 12:699-702 (1994)).

Alternatively, insects, such as the silkworm, may be used. A DNA encoding a desired protein inserted into baculovirus can be used to transfect silkworms, and the desired protein may be recovered from their body fluid (Susumu M. et al. Nature 315: 592-594 (1985)).

As plants, for example, tobacco can be used. When using tobacco, a DNA encoding a desired protein may be inserted into a plant expression vector such as pMON530, which is introduced into bacteria such as Agrobacterium tumefaciens. Then, the bacteria are used to transfect a tobacco plant such as Nicotiana tabacum, and a desired polypeptide is recovered from the leaves (Julian K. -C. Ma et al., Eur. J. Immunol. 24: 131-138 (1994)).

A protein of the present invention obtained as above may be isolated from the inside or outside (such as culture medium) of host cells, and purified as a substantially pure homogeneous protein. The method for protein isolation and purification is not limited to any specific method, and any standard method may be used. For instance, column chromatography, filter, ultrafiltration, salt precipitation, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the protein.

Examples of chromatographies include, for example, affinity chromatography, ion-exchange chromatography, hydrophobic chromatography, gel filtration, reverse phase chromatography, adsorption chromatography, and such (Strategies for Protein Purification and Characterization: A Laboratory Course Manual. Ed. Daniel R. Marshak et al., Cold Spring Harbor Laboratory Press (1996)). These chromatographies may be performed by a liquid chromatography such as HPLC and FPLC. Thus, the present invention provides highly purified proteins prepared by the above methods.

A protein of the present invention may be optionally modified or partially deleted by treating it with an appropriate protein modification enzyme before or after purification. Useful protein modification enzymes include, but are not limited to, trypsin, chymotrypsin, lysylendopeptidase, protein kinase, glucosidase and so on.

The present invention provides antibodies that bind to the proteins of the invention. The antibodies can take any form such as monoclonal or polyclonal antibodies, and includes antiserum obtained by immunizing an animal such as a rabbit with a protein of the invention, all classes of polyclonal and monoclonal antibodies, human antibodies, and humanized antibodies produced by genetic recombination.

A protein of the invention used as an antigen to obtain an antibody may be derived from any animal species, but is preferably derived from a mammal such as a human, mouse, or rat, more preferably a human. A human-derived protein may be obtained from the nucleotide or amino acid sequences disclosed herein.

According to the present invention, the protein to be used as an immunization antigen may be a complete protein or a partial peptide of the protein. A partial peptide may comprise, for example, the amino (N)-terminal or carboxy (C)-terminal fragment of a protein of the present invention. Herein, an antibody is defined as a protein that reacts with either the whole protein of the present invention, or a fragment of the protein.

A gene encoding a protein of the invention or its fragment may be inserted into a known expression vector, which is then used to transform a host cell as described herein. The desired protein or its fragment may be recovered from the outside or inside of host cells by any standard method, and may subsequently be used as an antigen. Alternatively, cells expressing the protein or their lysates, or a chemically synthesized protein may be used as the antigen. In the case of a short peptide, it is preferably bound to an appropriate carrier protein such as keyhole limpet hemocyanin, bovine serum albumin, and ovalbumin before using as antigen.

Any mammalian animal may be immunized with the antigen, but preferably, the compatibility with parental cells used for cell fusion is taken into account. In general, animals of Rodentia, Lagomorpha, or Primates are used.

Animals of Rodentia include, for example, mice, rats, and hamsters. Animals of Lagomorpha include, for example, rabbits. Animals of Primates include, for example, monkeys of Catarrhini (old world monkeys) such as *Macaca fascicularis*, rhesus monkeys, sacred baboons, and chimpanzees.

Methods for immunizing animals with antigens are known in the art. Intraperitoneal injection or subcutaneous injection of antigens is a standard method of immunization for mammals. More specifically, antigens may be diluted and suspended in an appropriate amount of phosphate buffered saline (PBS), physiological saline, etc. If desired, the antigen suspension may be mixed with an appropriate amount of a standard adjuvant such as Freund's complete adjuvant, made into an emulsion, and then administered to mammalian animals. Preferably, this is followed by several administrations of antigen mixed with an appropriately amount of Freund's incomplete adjuvant every 4 to 21 days. An appropriate carrier may also be used for immunization. After immunizing as above, serum is examined by a standard method for an increase in the amount of desired antibodies.

Polyclonal antibodies against the proteins of the present invention may be prepared by collecting blood from the immunized mammal after verifying an increase of desired antibodies in the serum, and by separating serum from the blood by any conventional method. Polyclonal antibodies include serum containing polyclonal antibodies, as well as fractions containing the polyclonal antibodies isolated from the serum. Immunoglobulin G or M can be prepared from a fraction which recognizes only the protein of the present invention using, for example, an affinity column coupled with a protein of the present invention, and further purifying this fraction using a protein A or protein G column.

To prepare monoclonal antibodies, immunocytes are collected from the mammal immunized with the antigen and checked for an increase in the level of desired antibodies in the serum as described above, and are subjected to cell fusion. The immune cells used for cell fusion are preferably obtained from the spleen. Other preferred parental cells to be fused with the above immunocytes include, for example, mammalian myeloma cells, and more preferably myeloma cells having an acquired property for the selection of fused cells by drugs.

The above immunocytes and myeloma cells can be fused according to known methods, for example, the method of Milstein et al. (Galfre, Q and Milstein, C., Methods Enzymol. (1981) 73, 346).

Resulting hybridomas obtained by the cell fusion may be selected by cultivating them in a standard selection medium such as the HAT medium (hypoxanthine, aminopterin, and thymidine containing medium). The cell culture is typically continued in the HAT medium for several days to several weeks, which is sufficient to allow all the other cells, with the exception of the desired hybridoma (non-fused cells), to die. Then, standard limiting dilution is performed to screen and clone a hybridoma producing the desired antibody.

In addition to the above method in which a non-human animal is immunized with an antigen for preparing a hybridoma, a hybridoma producing a desired human antibody that is able to bind to a protein can be obtained by the following method. First, human lymphocytes such as those infected by the EB virus may be immunized with a protein, protein expressing cells, or their lysates in vitro. Then, the immunized lymphocytes are fused with human-derived myeloma cells that are capable of indefinite division, such as U266, to yield the desired hybridoma (Unexamined Published Japanese Patent Application No. (JP-A) Sho 63-17688).

The obtained hybridomas are subsequently transplanted into the abdominal cavity of a mouse and the ascites are harvested. The obtained monoclonal antibodies can be purified by, for example, ammonium sulfate precipitation, a protein A or protein G column, DEAE ion exchange chromatography, or an affinity column to which a protein of the present invention is coupled. The antibodies of the present invention can be used not only for purification and detection of the proteins of the present invention, but also as candidates for agonists and antagonists of the proteins. In addition, these antibodies can be applied to the antibody treatment for diseases related to the proteins of the present invention. When an obtained antibody is to be administered to the human body (antibody treatment), a human antibody or a humanized antibody is preferable to reduce immunogenicity.

For example, transgenic animals having a repertoire of human antibody genes may be immunized with an antigen selected from a protein, cells expressing the protein or their lysates. Antibody producing cells are then collected from the animals and fused with myeloma cells to obtain hybridomas, from which human antibodies against the protein can be prepared (see WO92-03918, WO93-2227, WO94-02602, WO94-25585, WO96-33735, and WO96-34096).

Alternatively, an immunocyte that produces antibodies, such as an immunized lymphocyte, may be immortalized by an oncogene and used for preparing monoclonal antibodies.

Monoclonal antibodies thus obtained can also be recombinantly prepared using genetic engineering techniques (see, for example, Borrebaeck C. A. K. and Larrick J. W. Therapeutic Monoclonal Antibodies, published in the United Kingdom by MacMillan Publishers LTD (1990)). A DNA encoding an antibody may be cloned from an immunocyte, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the proteins of the invention. For instance, the antibody fragment may be Fab, F(ab')$_2$, Fv, or single chain Fv (scFv), in which Fv fragments from H and L chains are ligated by an appropriate linker (Huston J. S. et al. Proc. Natl. Acad. Sci. U.S.A. 85:5879-5883 (1988)). More specifically, an antibody fragment may be generated by treating an antibody with an enzyme such as papain or pepsin. Alternatively, a gene encoding the antibody fragment may be constructed, inserted into an expression vector, and expressed in an appropriate host cell (see, for example, Co M. S. et al. J. Immunol. 152:2968-2976 (1994); Better M. and Horwitz A. H. Methods Enzymol. 178:476-496 (1989); Pluckthun A. and Skerra A. Methods Enzymol. 178:497-515 (1989); Lamoyi E. Methods Enzymol. 121:652-663 (1986); Rousseaux J. et al. Methods Enzymol. 121:663-669 (1986); Bird R. E. and Walker B. W. Trends Biotechnol. 9:132-137 (1991)).

An antibody may be modified by conjugation with a variety of molecules, such as polyethylene glycol (PEG). The present invention provides such modified antibodies. The modified antibody can be obtained by chemically modifying an antibody. These modification methods are conventional in the field.

Alternatively, an antibody of the present invention may be obtained as a chimeric antibody between a variable region derived from a nonhuman antibody and a constant region derived from a human antibody. It can also be obtained as a humanized antibody comprising a complementarity-determining region (CDR) derived from a nonhuman antibody, a frame work region (FR) and a constant region derived from a human antibody. Such antibodies can be prepared using a known technology.

Antibodies obtained as above may be purified to homogeneity. For example, the separation and purification of the antibody can be performed according to separation and purification methods used for general proteins. For example, the antibody may be separated and isolated by appropriately selecting and combining column chromatographies such as affinity chromatography, filter, ultrafiltration, salting-out, dialysis, SDS polyacrylamide gel electrophoresis, isoelectric focusing, and others (Antibodies: A Laboratory Manual. Ed Harlow and David Lane, Cold Spring Harbor Laboratory, 1988), but the chromatographies are not limited thereto. The concentration of the thus obtained antibodies can be determined by measuring the absorbance, by an enzyme-linked immunosorbent assay (ELISA), and so on.

A protein A column or protein G column can be used as the affinity column. Examples of protein A columns include, for example, Hyper D, POROS, and Sepharose F.F. (Pharmacia).

Examples of chromatographies other than affinity chromatography includes, for example, ion-exchange chromatography, hydrophobic chromatography, gel filtration, reverse-phase chromatography, adsorption chromatography, and the like (Strategies for Protein Purification and Characterization: A Laboratory Course Manual. Ed Daniel R. Marshak et al., Cold Spring Harbor Laboratory Press, 1996). The chromatographies can be carried out by a liquid-phase chromatography, such as HPLC, FPLC.

For example, measurement of absorbance, enzyme-linked immunosorbent assay (ELISA), enzyme immunoassay (EIA), radioimmunoassay (RIA), and/or immunofluorescence may be used to measure the antigen binding activity of an antibody of the invention. In ELISA, an antibody of the present invention is immobilized on a plate, a protein of the invention is applied to the plate, and then a sample containing a desired antibody, such as a culture supernatant of antibody producing cells or purified antibodies, is applied. Then, a secondary antibody that recognizes the primary antibody and is labeled with an enzyme such as alkaline phosphatase is applied, and the plate is incubated. Next, after washing, an enzyme substrate such as p-nitrophenyl phosphate is added to the plate, and the absorbance is measured to evaluate the antigen binding activity of the sample. A fragment of the protein, such as a C-terminal fragment may be used as the protein. BIAcore (Pharmacia) may be used to evaluate the activity of an antibody according to the present invention.

These methods allow the detection or measurement of a protein of the invention by exposing an antibody of the invention to a sample assumed to contain the protein of the invention, and detecting or measuring the immune complex formed by the antibody and the protein. Because the method of detection or measurement of the protein according to the invention can specifically detect or measure a protein, the method may be useful in a variety of experiments in which the protein is used.

Furthermore, the present invention provides a polynucleotide comprising at least 15 nucleotides, which is complementary to a DNA encoding the MC-PIR1 or MC-PIR2 protein (comprising the nucleotide sequence according to SEQ ID NO: 1 or 3) or a complementary strand thereof.

Herein, "complementary strand" means a strand that is opposite relative to the other strand in a double-stranded nucleic acid composed of A:T (U in the case of RNA) and G:C base pairs. In addition, being "complementary" is not limited to having completely complementarity in a continuous region of at least 15 nucleotides, but it can also mean having a homology of at least 70%, preferably at least 80%, more preferably 90%, and most preferably 95% or higher at the nucleotide level. Homology can be determined using the algorithm described herein.

Such nucleic acids include: probes or primers used for detecting or amplifying a DNA encoding a protein of this invention; probes or primers used for detecting DNA expression; or nucleotides or nucleotide derivatives (for example, antisense oligonucleotides or ribozymes, or DNA encoding them) used for regulating the expression of a protein of this invention. Such nucleic acids may also be useful for preparing DNA chips.

When using as a primer, the 3'-region can be made complementary and a recognition site for a restriction enzyme, or a tag can be attached to the 5'-region.

Antisense oligonucleotides include, for example, those that hybridize with any site in the nucleotide sequence of SEQ ID NO: 1 or 3. Such antisense oligonucleotides are preferably complementary to at least 15 or more continuous nucleotides in the sequence of SEQ ID NO: 1 or 3. More preferably, they are complementary to at least 15 or more continuous nucleotides comprising the translation initiation codon in the sequence.

Derivatives or modified forms of antisense oligonucleotides can be used as antisense oligonucleotides. For example, modified antisense oligonucleotides include lower alkylphosphonate modified forms such as the methylphosphonate type or ethylphosphonate type, or phosphorothioate modified forms, phosphoroamidate modified forms, or the like.

Antisense oligonucleotides are not limited to those in which the entire nucleotide sequence corresponding to a nucleotide sequence composing a certain DNA or mRNA region is completely complementary. One or more nucleotide mismatches may be contained as long as the antisense oligonucleotide specifically hybridizes with the nucleotide sequence shown in SEQ ID NO: 1 or 3.

The antisense oligonucleotide derivatives or modified forms of the present invention act upon cells producing a protein of the invention by binding to the DNA or mRNA encoding the protein, inhibiting its transcription or translation, promoting the degradation of the mRNA, and inhibiting the expression of the protein, thereby resulting in the inhibition of the protein's function.

An antisense oligonucleotide derivative or modified form of the present invention can be made into an external preparation, such as a liniment or a poultice, by mixing with a suitable base material which is inactive against the derivative or modified form.

Also, as needed, the derivatives or modified forms can be formulated into tablets, powders, granules, capsules, liposome capsules, injections, solutions, nose-drops, and freeze-drying agents by adding excipients, isotonic agents, solubilizers, stabilizers, preservatives, pain-killers, and such. These can be prepared by following usual methods.

The antisense oligonucleotide derivatives or modified forms are given to a patient by directly applying them onto the ailing site or by injecting them into a blood vessel so that they will reach the site of ailment. An antisense-mounting medium can also be used to increase durability and membrane-permeability. Examples are, liposomes, poly-L-lysine, lipids, cholesterol, lipofectin or derivatives of these.

The dosage of an antisense oligonucleotide derivative or modified form of the present invention can be suitably adjusted according to the patient's condition and used in desired amounts. For example, a dose range of 0.1 to 100 mg/kg, preferably 0.1 to 50 mg/kg can be administered.

The antisense oligonucleotides of the invention inhibits the expression of a protein of the invention and is thereby useful for suppressing the biological activity of the protein. Also, expression-inhibitors comprising an antisense oligonucleotide of the invention are useful in that they can inhibit the biological activity of a protein of the invention.

The proteins of this invention may be useful for screening compounds capable of binding to the proteins. Specifically, the proteins can be used in methods of screening for compounds capable of binding to the proteins, comprising the steps of contacting a protein of the invention and a test sample that is expected to contain such a compound, and then selecting the compound.

The protein of the invention used for the screening may be a recombinant protein or naturally-occurring protein. It may also be a partial peptide. It can be expressed on the cell surface, or contained in the membrane fraction. The test sample is not limited to any particular sample; it can be, for example, a cell extract, a cell culture supernatant, a product of a fermentation microorganism, a marine organism extract, a plant extract, a purified or crude protein, a peptide, a non-peptide compound, a synthetic low molecular weight compound, or a natural compound. The protein of this invention can be contacted with the test sample as a purified protein, soluble protein, in a form bound to a carrier, as a fusion protein with another protein, in a form expressed on the cell surface, or as a form contained in the membrane fraction.

As a method of screening for proteins that, for example, bind to a protein of the present invention using a protein of the present invention, many methods well known to those skilled in the art can be used. Such a screening can be conducted by, for example, the immunoprecipitation method, specifically, in the following manner. A gene encoding a protein of the present invention is expressed in animal cells, or such, by inserting the gene into an expression vector for foreign genes, such as pSV2neo, pcDNA I, and pCD8. The promoter to be used for the expression may be any promoter that can generally be used and include, for example, the SV40 early promoter (Rigby in Williamson (ed.), Genetic Engineering, vol. 3. Academic Press, London, p. 83-141 (1982)), the EF-1α promoter (Kim et al., Gene 91, p217-223 (1990)), the CAG promoter (Niwa et al. Gene 108, p. 193-200 (1991)), the RSV LTR promoter (Cullen Methods in Enzymology 152, p. 684-704 (1987)) the SRα promoter (Takebe et al., Mol. Cell. Biol. 8, p. 466 (1988), the CMV immediate early promoter (Seed and Aruffo Proc. Natl. Acad. Sci. USA 84, p. 3365-3369 (1987)), the SV40 late promoter (Gheysen and Fiers J. Mol. Appl. Genet. 1, p. 385-394 (1982)), the Adenovirus late promoter (Kaufman et al., Mol. Cell. Biol. 9, p. 946 (1989)), the HSV TK promoter and so on.

The introduction of the gene into animal cells to express a foreign gene can be performed according to any method, for example, the electroporation method (Chu G et al. Nucl. Acids Res. 15, 1311-1326 (1987)), the calcium phosphate method (Chen, C and Okayama, H. Mol. Cell. Biol. 7, 2745-2752 (1987)), the DEAE dextran method (Lopata, M. A. et al. Nucl. Acids Res. 12, 5707-5717 (1984)), Sussman, D. J. and Milman, G. Mol. Cell. Biol. 4, 1642-1643 (1985)), the Lipofectin method (Derijard, B. Cell 7, 1025-1037 (1994); Lamb, B. T. et al. Nature Genetics 5, 22-30 (1993): Rabindran, S. K. et al. Science 259, 230-234 (1993)), and so on.

A protein of the present invention can be expressed as a fusion protein comprising a recognition site (epitope) of a monoclonal antibody by introducing, to the N- or C-terminus of the protein, an epitope of a monoclonal antibody whose specificity has been revealed. A commercially available epitope-antibody system can be used (Experimental Medicine 13, 85-90 (1995)). Vectors that can express a fusion protein with, for example, p-galactosidase, maltose-binding protein, glutathione S-transferase, green florescence protein (GFP) and so on through multiple cloning sites are commercially available.

A method of preparing a fusion protein by introducing only a small epitope portion consisting of several to a dozen amino acids so as to not change, as much as possible, the property of the protein of the present invention by the fusion, has also been reported. Epitopes, such as polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), E-tag (an epitope on monoclonal phage), and such, and monoclonal antibodies recognizing them can be used as epitope-antibody systems for screening proteins binding to the proteins of the present invention (Experimental Medicine 13, 85-90 (1995)).

In immunoprecipitation, an immune complex is formed by adding these antibodies to a cell lysate prepared by using an appropriate detergent. The immune complex consists of a protein of the present invention, a protein that can bind with the protein, and an antibody. Immunoprecipitation can also be conducted by using antibodies against a protein of the present invention, besides using antibodies against the above epitopes. An antibody against a protein of the present invention can be prepared, for example, by introducing a gene encoding the protein into an appropriate E. coli expression vector, expressing the gene in E. coli, purifying the expressed protein, and immunizing rabbits, mice, rats, goats, chicken and such with the protein. The antibody can be also prepared by immunizing an animal of above with a synthesized partial peptide of the protein of the present invention.

An immune complex can be precipitated, for example by Protein A Sepharose or Protein G sepharose when the antibody is a mouse IgG antibody. If the proteins of the present invention are prepared as fusion proteins with an epitope such as GST, an immune complex can be formed in the same manner as when using the antibody against a protein of the present invention, by using a substance that specifically binds to the epitope, such as glutathione-Sepharose 4B.

Immunoprecipitation can be performed by following or according to, for example, methods in literature (Harlow, E. and Lane, D.: Antibodies pp. 511-552, Cold Spring Harbor Laboratory publications, New York (1988)).

SDS-PAGE is commonly used for analyzing immunoprecipitated proteins. The bound protein can be analyzed by the molecular weight of the protein using a gel with an appropriate concentration. Since the protein bound to the protein of the present invention is difficult to detect by a common staining method such as Coomassie staining or silver staining, the detection sensitivity of the protein can be improved by culturing cells in a culture medium containing the radioactive isotope $^{35}$S-methionine or $^{35}$S-cystein, labeling proteins within the cells, and detecting the proteins. Once the molecular weight of the protein has been revealed, the target protein can be purified directly from the SDS-polyacrylamide gel and its sequence can be determined.

In addition, as a method for isolating a protein capable of binding to the protein using a protein of this invention, western blotting may be used (Skolnik E. Y. et al. Cell 65: 83-90 (1991)). Specifically, a cDNA library using a phage vector (λgt11, ZAP, and the like) can be prepared using a cell, tissue, or organ expected to express a protein capable of binding to the protein of this invention (for example, adipocytes or tissues where the expression is detected by northern blotting in the Examples). Then, the cDNA library can be expressed on LB-agarose, expressed protein immobilized onto a filter, the protein of this invention, which is purified and labeled, incubated with the above filter, and the plaque expressing the protein capable of binding to the protein of this invention detected by the label. For labeling the protein of this invention, methods that make use of: the binding between biotin and avidin; an antibody specifically binding to the protein of this invention, or a peptide or polypeptide fused to the protein (for example, GST); radioisotopes; or fluorescence, or the like, can be used.

In another embodiment of the screening methods of this invention, the two-hybrid system using cells may be used (Fields S. and Sternglanz R. Trends Genet. 10: 286-292 (1994); Dalton S. and Treisman R. Characterization of SAP-1, a protein recruited by serum response factor to the c-fos serum response element. Cell 68: 597-612 (1992); "MATCH-MAKER Two-Hybrid System"; "Mammalian MATCH-MAKER Two-Hybrid Assay Kit"; "MATCHMAKER One-Hybrid System" (all from Clontech); and "HybriZAP Two-Hybrid Vector System" (Stratagene)). In the two-hybrid system, a protein of this invention or a partial peptide may be expressed in yeast cells as a fusion protein with the SRF DNA binding domain, or GAL4 DNA binding domain. A cDNA library in which the protein is expressed as a fusion between the VP16 or GAL4 transcription activation domain is prepared from cells in which a protein capable of binding to a protein of this invention is expected to be present. The library is transfected into yeast cells, and cDNA derived from the library is isolated from a positive clone detected (when a protein capable of binding to the protein of this invention is expressed in yeast cells, binding of the two proteins activates a reporter gene, which is used to detect a positive clone). Isolated cDNA may be introduced and expressed in E. coli to obtain a protein encoded by the cDNA. The reporter gene used in the two-hybrid system may be, for example, a gene such as HIS3, Ade2, LacZ, CAT, luciferase, and PAI-1 (plasminogen activator inhibitor type I), but is not limited thereto. Such a screening using the two-hybrid system may be performed using a mammalian cell other than yeast.

A compound binding to a protein of the present invention can be screened using affinity chromatography. For example, the protein of the invention may be immobilized on a carrier of an affinity column, and a test sample presumed to express a protein capable of binding to the protein of the invention, is applied to the column. Herein, a test sample may be, for example, a cell extract, cell lysate, etc. After loading the test sample, the column is washed, and proteins bound to the protein of the invention can be prepared.

The amino acid sequence of the obtained protein is analyzed, an oligo DNA is synthesized based on the sequence, and cDNA libraries are screened using the oligo DNA as a probe to obtain a DNA encoding the protein.

A biosensor using the surface plasmon resonance phenomenon may be used as a means for detecting or quantifying the bound compound in the present invention. When such a biosensor is used, the interaction between the protein of the invention and a test compound can be observed real-time as a surface plasmon resonance signal, using only a minute amount of protein and without labeling (for example, BIAcore, Pharmacia). Therefore, it is possible to evaluate the binding between the protein of the invention and a test compound using a biosensor such as BIAcore.

The methods of screening for molecules that bind when the immobilized protein of the present invention is exposed to synthetic chemical compounds, or natural substance banks, or a random phage peptide display library, or the methods of screening using high-throughput based on combinatorial chemistry techniques (Wrighton Nc, Farrel F X, Chang R, Kashyap A K, Barbone F P, Mulcahy L S, Johnson D L, Barret R W, Jolliffe L K, Dower W J; Small peptides as potent mimetics of the protein hormone erythropoietin, Science (UNITED STATES) Jul. 26, 1996, 273 p 458-64, Verdine G L., The combinatorial chemistry of nature. Nature (ENGLAND) Nov. 7, 1996, 384, p 11-13, Hogan J C Jr., Directed combinatorial chemistry. Nature (ENGLAND) Nov. 7, 1996, 384 p17-9) to isolate not only proteins but chemical compounds that bind to a protein of the present invention (including agonists and antagonists) are well known to those skilled in the art.

In addition, the present inventors demonstrated that the proteins of this invention are capable of binding to SHP-1, SHP-2, SHIP, DAP10, DAP12, or FcRγ protein. Thus, using the above described immunoprecipitation or the two-hybrid system, the binding ability between a protein of this invention and SHP-1, SHP-2, SHIP, DAP10, DAP12, or FcRγ protein in the presence of a test sample can be detected, and a substance with the ability to reduce the binding may be selected to screen for a candidate for a medicinal compound. Thus, the present invention provides a screening method comprising the steps of contacting a protein of this invention with a protein selected from the group consisting of SHP-1, SHP-2, SHIP, DAP 10, DAP12, and FcRγ proteins in the presence of a test sample, detecting the binding activity, and selecting a substance capable of reducing the binding activity by comparing with the activity detected in the absence of the test sample.

Such compounds isolated using the screening methods of this invention can be candidates of therapeutic agents for regulating the activity of a protein of this invention. They may be useful in applications such as treatment of diseases caused by abnormal function or abnormal expression of the protein, or diseases that can be treated by regulating the activity of the protein. Such diseases include allergic diseases such as atopic dermatitis, rhinitis, and asthma. Also included in the compounds capable of binding to proteins of this invention are substances in which a part of the structure of a compound isolated using a screening method is modified by addition, deletion, and/or substitution.

When administrating a protein of this invention or a compound isolated by a screening method of the invention as a pharmaceutical for humans and other mammals such as mice, rats, guinea-pigs, rabbits, chicken, cats, dogs, sheep, pigs, cattle, monkeys, baboons and chimpanzees, the protein or the isolated compound can be directly administered or formulated into a dosage form using known pharmaceutical preparation methods. For example, according to the need, the pharmaceutical can be taken orally, as a sugar-coated tablet, capsule, elixir or microcapsule, or non-orally, in the form of an injection of a sterile solution or suspension with water or any other pharmaceutically acceptable liquid. For example, the compounds can be mixed with pharmacologically acceptable carriers or medium, specifically, sterilized water, physiological saline, plant oils, emulsifiers, suspending agents, surfactants, stabilizers, flavoring agents, excipients, vehicles, preservatives, binders and such, in a unit dose form required for generally accepted drug implementation. The amount of active ingredient in these preparations facilitates the acquisition of a suitable dosage within the indicated range.

Examples of additives that can be mixed to tablets and capsules are, binders such as gelatin, corn starch, tragacanth gum and arabic gum; excipients such as crystalline cellulose; swelling agents such as corn starch, gelatin and alginic acid; lubricants such as magnesium stearate; sweeteners such as sucrose, lactose or saccharin; flavoring agents such as peppermint, Gaultheria adenothrix oil and cherry. When the unit dosage form is a capsule, a liquid carrier such as oil can also be included in the above ingredients. Sterile composites for injections can be formulated following normal drug implementations using vehicles such as distilled water used for injections.

Physiological saline, glucose, and other isotonic liquids including adjuvants such as D-sorbitol, D-mannnose, D-mannitol, and sodium chloride, can be used as aqueous solutions for injections. These can be used in conjunction with suitable solubilizers such as alcohol, specifically ethanol, polyalcohols such as propylene glycol and polyethylene glycol, and non-ionic surfactants such as Polysorbate 80 (TM) and HCO-50.

Sesame oil or Soy-bean oil can be used as a oleaginous liquid and may be used in conjunction with benzyl benzoate or benzyl alcohol as a solubilizer and may be formulated with a buffer such as phosphate buffer and sodium acetate buffer; a pain-killer, such as procaine hydrochloride; a stabilizer, such as benzyl alcohol, phenol; and an anti-oxidant. The prepared injection may be filled into a suitable ampule.

Methods well known to those skilled in the art may be used to administer the inventive pharmaceutical to patients, for example as intraarterial, intravenous, percutaneous injections and also as intranasal, transbronchial, intramuscular, percutaneous, or oral administrations. The dosage and method of administration vary according to the body weight and age of the patient and the administration method; however, these can be routinely selected by one skilled in the art. If said compound is encodable by a DNA, the DNA can be inserted into a vector for gene therapy and the vector administered to perform the therapy. The dosage and method of administration vary according to the body weight, age, and symptoms of the patient, but one skilled in the art can select them suitably.

The dose per time of a protein of this invention may vary depending on the type of recipient, target organ, disease condition, and administration method. For example, when injecting into a normal adult (body weight: 60 kg), it may be administered at about 100 μg to 20 mg per day.

The dose of a compound that binds to a protein of this invention, or that of a compound that regulates the activity of a protein of this invention vary depending on the type of disease. For example, the compound may be administered orally into a normal adult (body weight: 60 kg) at about 0.1 to 100 mg per day, preferably at about 1.0 to 50 mg per day, and more preferably at about 1.0 to 20 mg per day.

When administered parenterally, the dose per time may vary depending on the recipient, target organ, disease condition, and administration method. For example, an appropriate dose can be, as an intravenous injection into a normal adult (body weight: 60 kg), usually about 0.01 to 30 mg per day, preferably about 0.1 to 20 mg per day, and more preferably about 0.1 to 10 mg per day. For other animals, an amount converted to dose per 60 kg body weight, or dose per body surface area may be applied.

BRIEF DESCRIPTION OF THE DRAWINGS

FIG. 1 shows the nucleotide sequence of the MC-PIR1 cDNA (SEQ ID NO:1) and its deduced amino acid sequence (SEQ ID NO:2). Dotted line under the nucleotide sequence indicates the DNA fragment isolated by the SST-REX method. Poly-A signal is shown by the underline at the bottom. The signal sequence is indicated by lower case letters. Thickened underline shows the transmembrane domain. The ITIM sequences are shown by doubled underlines. Cysteines participating in S-S bond formation are boxed. The binding sequence for the asparagine-linked sugar chain is also boxed.

FIG. 2 shows the open-reading frame of MC-PIR2 (SEQ ID NO:3) and its deduced amino acid sequence (SEQ ID NO:4). The signal sequence is shown by lower case letters. The transmembrane domain is indicated by thickened underline. The lysine residue critical for binding to other cofactor molecule containing the ITAM sequence in the transmembrane domain is boxed. Cysteines participating in S-S bond formation are also boxed. The binding sequence for the asparagine-linked sugar chain is also boxed.

FIG. 3 is a photograph showing the result of a PCR analysis of MC-PIR1 and MC-PIR2 expression in different tissues. GAPDH was used as a control.

FIG. 7 an electrophoresis photograph showing the result of complex formation with phosphotyrosine phosphatase SHP-1 and SHP-2, and phosphoinositide phosphatase SHIP.

BEST MODE FOR CARRYING OUT THE INVENTION

Figure 4:
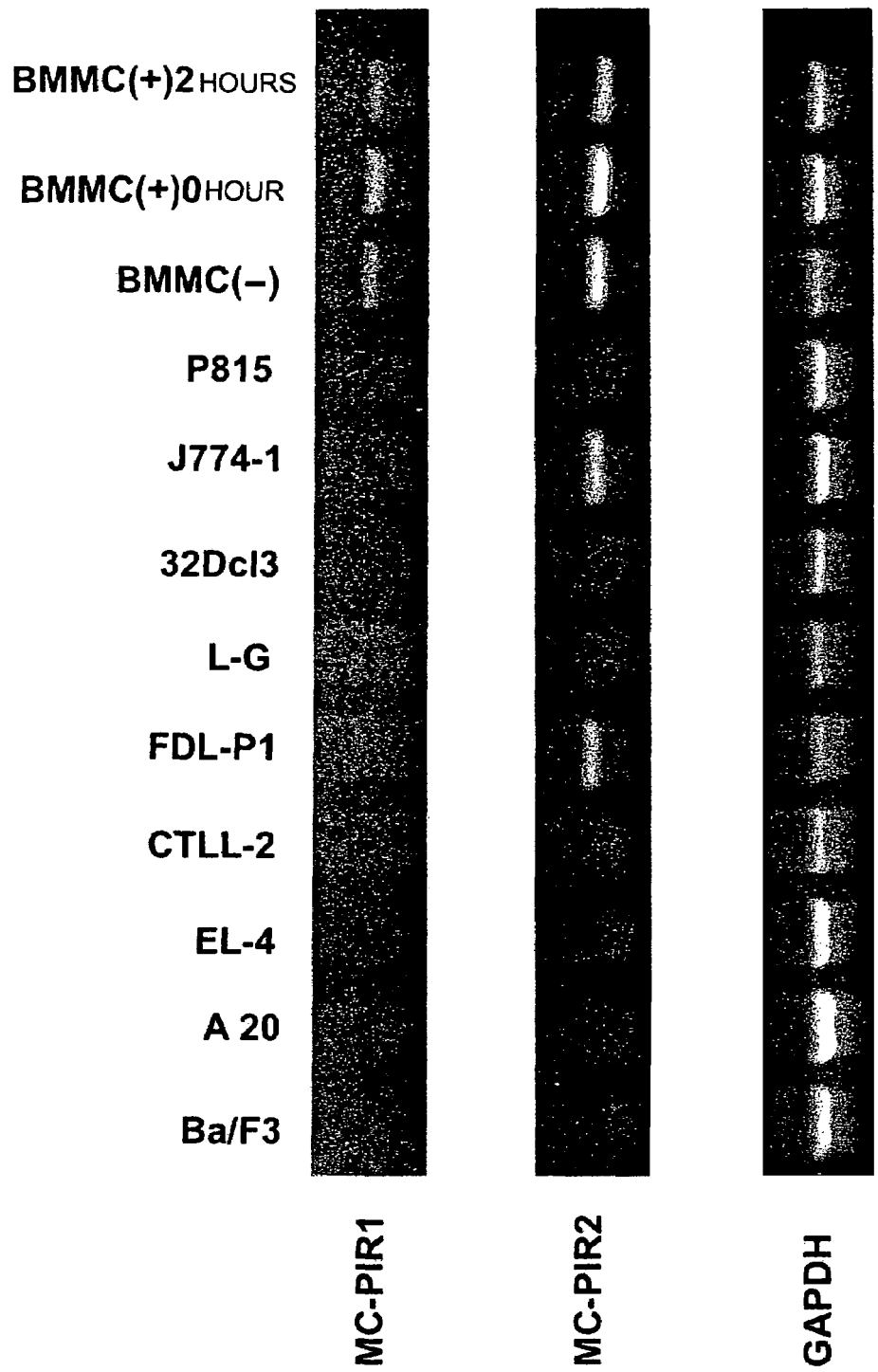
FIG. 4 is a photograph showing the result of an RT-PCR analysis of MC-PIR1 and MC-PIR2 expression in different cell types. GAPDH was used as a control.

This invention will be explained in detail below with reference to Examples, but it is not to be construed as being limited thereto.

EXAMPLE 1

Construction of a cDNA Library and Screening

A cDNA library was constructed and expressed using the retrovirus vector pMX-SST (Kojima T. and Kitamura T. Nature Biotechnol. 17: 487-490 (1999)).

Poly-A(+) RNA was extracted from mast cells derived from mouse bone marrow, stimulated with antigen using the Fast track 2.0 mRNA extraction kit (Invitrogen, Carlsbad, Calif.) according to the manufacturer's protocol.

cDNA was synthesized from poly-A(+) RNA using the SuperScript Choice System (Invitrogen) and random hexamers, and inserted into the BstXI site of pMX-SST vector using a BstXI adaptor (Invitrogen). To construct a SST-REX library, ligated DNA was amplified in DH10B cells (ElectroMax, Invitrogen), and library DNA was prepared using the Qiagen plasmid kit (Qiagen Inc., Valencia, Calif.). The size of the cDNA library was $2.0 \times 10^6$ clones.

High titer retroviruses presenting the SST-REX library was produced using the Plat-E packaging cell line (Morita S. et al. Gene Therapy 7: 1063-1066 (2000)), and used for infection of Ba/F3 cells as described. The day following infection, cells were washed three times, seeded in 96-well multi titer plates ($10^3$ cells/well), and clones were selected in the absence of IL-3.

After twelve days, genomic DNA was extracted from factor independent Ba/F3 clones, and subjected to genomic PCR using vector primers to recover inserted cDNA (GGGGGTGGACCATCCTCTA/SEQ ID NO: 5; and CGCGCAGCTGTAAACGGTAG/SEQ ID NO: 6). PCR was performed on GeneAmp PCR system 480 (Perkin Elmer, Norfolk, Conn.) using LA Taq polymerase (TaKaRa, Kyoto, Japan) in 30 cycles (each cycle consisting of denaturation at 98° C. for 20 seconds, followed by annealing and extension at 68° C. for 2 minutes). The obtained PCR fragment was processed for sequencing using the Taq Dye-Terminator Cycle Sequencing kit (Applied Biosystems Inc., Foster City, Calif.), and analyzed using an automated DNA sequencer (377 DNA analyzer; Applied Biosystems Inc.).

Differentiated cultured mast cells used in the experiment, which were derived from mouse bone marrow, were prepared as follows. Bone marrow cells were prepared from the thigh bone of CBA/JN mice, and cultured in RPMI 1640 supplemented with 10% FCS, 100 unit/ml of penicillin, 100 μg/ml of streptomycin, and 10 ng/ml of mouse IL-3 at 37° C., 5% $CO_2$. Cells were passaged every couple of days at a density of $5 \times 10^5$ cells, and maintained for four weeks to allow differentiation. Ba/F3 cells, a mouse IL-3 dependent pro B-cell line, were cultured in RPMI 1640 supplemented with 10% FCS, and 1 ng/ml of mouse IL-3 (R&D Systems).

Antigen stimulation of mast cells was performed as follows (Kawakami T. et al. J. Immunol. 148: 3513-3519 (1992)). Mast cells were challenged with 0.5 μg/ml of anti-DNP-IgE antibody (Sigma) overnight, and the next day, with 100 ng/ml of DNP-BSA (CosmoBio) for two hours.

EXAMPLE 2

Analysis of Isolated cDNA Clones

From the cDNA clones, a DNA fragment containing a signal sequence and encoding a single immunoglobulin domain was isolated.

A cDNA library was constructed using an oligo-dT primer. cDNA was synthesized from poly-A(+) RNA using the SuperScript Choice System (Invitrogen) and oligo-dT primer, and inserted into the BstXI site of pME18S vector using a BstXI adaptor (Invitrogen). To construct an oligo-dT cDNA library, ligated DNA was amplified in DH10B cells, and library DNA was prepared using the Qiagen plasmid purification kit (Qiagen Inc.). The size of the cDNA library was $1.5 \times 10^8$ clones.

Full-length cDNA was isolated by hybridization using RecA (Daiichi Kagaku Yakuhin, Tokyo, Japan). Using the isolated cDNA fragment as a template, PCR reaction was performed to synthesize a probe of approximately 500 bp, in which biotin 21-dUTP was incorporated (Clontech). The probe was hybridized with the oligo-dT cDNA library in the presence of RecA. DNA recovered using streptavidin magnetic beads (Promega) was amplified in DH10B cells (ElectroMax, Invitrogen), and E. coli clones were obtained. The E. coli clones were grown in a large scale, and DNA was prepared using the Qiagen plasmid kit (Qiagen Inc.). Purified DNA was processed for sequencing using the Taq Dye-Terminator Cycle Sequencing kit (Applied Biosystems Inc., Foster City, Calif.), and analyzed on an automated DNA sequencer (377 DNA analyzer; Applied Biosystems Inc.).

The obtained cDNA had a full length of 1752 bp, of which 957 nucleotides composed an open reading frame. The 3'-region, spanning 648 nucleotides, contained the poly-A-attaching signal. The deduced amino acid sequence contained 318 residues, in which a signal sequence of 27 amino acids, an extracellular domain of 156 amino acids, a transmembrane domain of 23 amino acids, and an intracellular domain of 112 amino acids were found. The extracellular domain had a single immunoglobulin domain of a variable type. The intracellular domain contained four ITIM-like sequences (FIG. 1). This gene was named MC-PIR1.

Genes having homology with this novel mouse gene are CMRF-35-H9 (CMRF-35H) (Green B. J. et al. Int. Immunol. 10: 891-899 (1998); Accession No. AF020314), and IRp60 (Cantoni C. et al. Eur. J. Immunol. 29: 3148-3159 (1999); Accession No. AJ224864). It is unknown, however, whether CMRF-35H or IRp60 is expressed in mast cells. According to the structural similarities, these genes are considered to be the human homologues of MC-PIR1.

The MC-PIR1 sequence was used to search EMBL/GenBank/DDBJ DNA databases. As a result, a DNA sequence (Accession No. BC006801) having approximately 90% homology with the immunoglobulin domain of MC-PIR1 was found. The sequence information was used to design primers, and RT-PCR was performed using total RNA prepared from mast cells. As a result, expression of a similar gene product was detected. Furthermore, the DNA fragment was recovered for sequence analysis.

As a result, a DNA having a sequence almost identical to that deposited in the DNA database (with two different bases at two sites compared to the sequence of Accession No. BC006801, resulting in two amino acid substitutions) was obtained, and named MC-PIR2 (FIG. 2). Later, it turned out that MC-PIR2 encodes exactly the same protein as DIgR1 (Luo K. et al. Biochem. Biophys. Res. Commun. 287: 35-41 (2001); Accession No. AY048685). The human gene CMRF-35A (Clark G J. et al. Tissue Antigens 57: 415-423 (2001); Accession No. BC022279) is homologous to this mouse gene. However it is not known whether or not DIgR1 or CMRF-35A is expressed in mast cells, or what functions they have therein.

EXAMPLE 3

Expression Profile of MC-PIR1 and MC-PIR2

Expression profile of the genes was analyzed by PCR. A commercial DNA, a cDNA synthesized from mRNA derived from different mouse tissues (Clontech), was used as a template for the PCR to amplify the DNA fragment. In addition, total RNA was prepared from a variety of hematopoietic lineage cell lines using the Trizol reagent (Invitrogen), and used to prepare cDNA using a reverse transcriptase (Qiagen). The cDNA was used as a template for PCR to amplify DNA fragment. Amplified DNA fragment was separated by electrophoresis on a 1% agarose gel.

Both MC-PIR1 and MC-PIR2 were expressed abundantly in the spleen and liver. For both, amplification of a specific DNA fragment was detected in mouse bone marrow-derived cultured mast cells (BMMC). Amplification of MC-PIR1 was not detected in other cell lines including Ba/F3, A20, EL4, CTLL-2, FDC-P1, L-G, 32Dc13, J774.1, and P815. Expression of MC-PIR2 was detected in J774.1 and FDC-P1 as well (FIGS. 3 and 4). The result suggests that MC-PIR1 and MC-PIR2 is directly involved in the regulation of mast cell function.

EXAMPLE 4

Expression of MC-PIR1 and MC-PIR2 on the Cell Surface of Mouse Bone Marrow-Derived Mast Cells Mast cells, prepared by the method in Example 1, were incubated with PE-labeled anti-CD117 monoclonal antibody (BD Pharmingen), and then with anti-MC-PIR1 mouse monoclonal antibody (custom made by R&D Systems) or anti-MC-PIR2 rabbit polyclonal antibody (custom made by Sigma Genosys). After washing, cells were incubated with FITC-labeled anti-mouse immunoglobulin antibody (BD Pharmingen), or FITC-labeled anti-rabbit immunoglobulin antibody (BD Pharmingen), respectively. After washing, cells were analyzed by FACS Calibur (Becton Dickinson).

Figure 5:
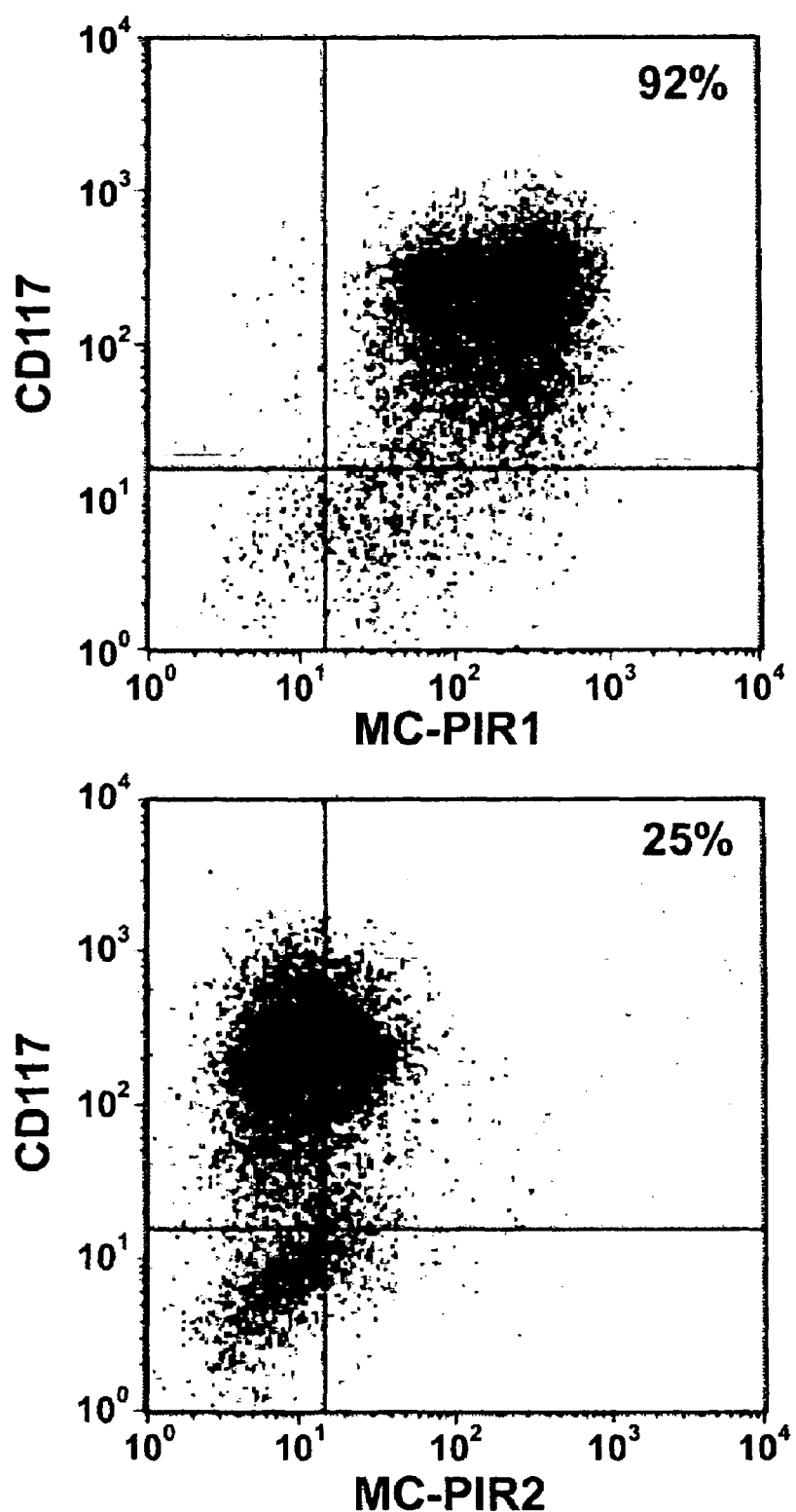
FIG. 5 shows the result of a FACS analysis indicating the presence of MC-PIR1 and MC-PIR2 on mast cell surface.

About 90% to 95% of prepared cells were positive for CD117, and almost all the cells were induced to become mast cells. In CD117 positive cells, 90% were MC-PIR1 positive, and 25% was MC-PIR2 positive (FIG. 5). The result indicates that both MC-PIR1 and MC-PIR2 are present on the mast cell surface.

EXAMPLE 5

Analysis of the Intracellular Domain of MC-PIR1

A chimeric gene between FcγRIIB and MC-PIR1 was constructed. A DNA fragment encoding the extracellular and transmembrane domains of FcγRIIB was amplified by PCR. Similarly, a DNA fragment encoding the intracellular domain of MC-PIR1 was amplified by PCR. The two fragments were mixed and used as a template for PCR to amplify a DNA fragment and construct a chimeric gene. Then, a chimeric DNA fragment was digested with EcoRI and NotI, and inserted into pMX-IRES-puro vector to construct pMX-IRES-puro-Fc-PIR1.

A high titer stock of retroviruses presenting pMX-IRES-puro-Fc-PIR1 was produced in the Plat-E packaging cell line and used to infect IIA1.6 cells, an FcγRIIB deficient cell line, as described (Jones B. et al. J. Immunol. 136: 348-356 (1986)). A day after infection, the medium was supplemented with 1 μg/ml of puromycin (Clontech), and the culture was continued for an additional week to obtain a cell line expressing the chimeric gene.

The cell line expressing the chimeric gene was incubated with an anti-mouse IgG antibody (Zymed) to cross-link B-cell receptor and the chimeric gene product expressed on the cell surface, harvested over a time course, and lysed in cell lysis buffer. 2.4G monoclonal antibody (Becton Dickinson) was added to the cell lysate and anti-rat IgG antibody-Sepharose beads, and an immune complex was precipitated. The pellet was treated with peptide N-glycosidase F (Daiichi Kagaku Yakuhin), and subjected to electrophoresis on a 10% polyacrylamide gel (PAGE).

The immune complex separated by PAGE was electrically transferred onto an Immobilon-P membrane (Millipore). The membrane was blocked with buffer containing 10% FCS, and then incubated successively with the 4G10 monoclonal antibody (UpState Biotechnology) and HRP-conjugated anti-mouse immunoglobulin antibody (Sigma). The signal was detected using chemiluminescence reagents (Pharmacia).

Similarly, cells expressing the chimeric gene were cross-linked, and a membrane was prepared as described. The membrane was incubated with an anti-SHP-1 antibody (Santa Cruz), anti-SHP-2 antibody (Santa Cruz), or anti-SHIP antibody. The detection was performed as described above.

Figure 6:
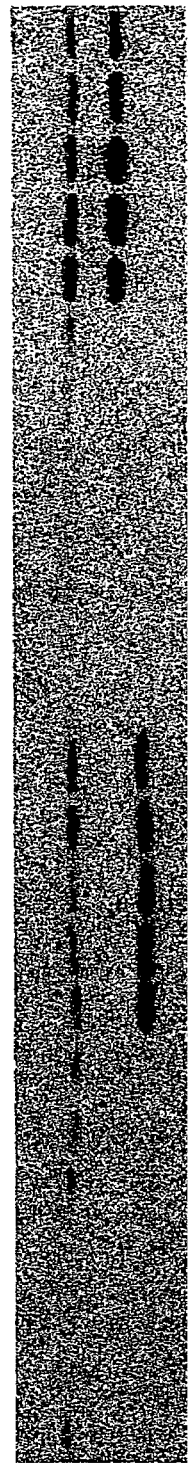
FIG. 6 is an electrophoresis photograph showing the result of tyrosine phosphorylation of a chimeric protein induced by cross-linking with anti-mouse IgG antibody.

Tyrosine phosphorylation of the chimeric protein was detected 0.5 minutes after cross-linking. Furthermore, an immune complex containing the chimeric protein was found containing SHP-1, SHP-2, and SHIP. The complex formation was dependent on tyrosine phosphorylation of the chimeric protein (FIGS. 6 and 7).

EXAMPLE 6

Complex Formation Between MC-PIR2 and ITAM-Comprising Signaling Molecules

MC-PIR2 was amplified by PCR using a primer attached with an HA tag at the C-terminal end. The obtained fragment was digested with EcoRI and NotI, and inserted into the pMKIT vector to construct pMKIT-MC-PIR2—HA.

The DNA fragment encoding a mature protein of ITAM sequence-comprising proteins DAP10, DAP12, or FcRγ was amplified by PCR. The amplified DNA fragment was digested with HindIII and NotI, and inserted into the downstream of the FLAG tag in the pMKIT-FLAG vector.

PMKIT-MC-PIR2-HA and either the pMKIT mock vector, FLAG-DAP10 vector, FLAG-DAP12 vector, or FLAG-FcRγ vector were transfected into COS1 cells. After two days, cells were harvested, and lysed in a cell lysis buffer. An anti-HA monoclonal antibody (12CA5, Roche Diagnostics), and Protein A-Sepharose beads were added to the cell lysate, and an immune complex was precipitated. The pellet was subjected to electrophoresis on a 15% polyacrylamide gel (PAGE). The immune complex separated by PAGE was electrically transferred onto an Immobilon-P membrane (Millipore). The membrane was blocked with a buffer containing 10% FCS, and then incubated successively with an anti-FLAG-M2 monoclonal antibody (Sigma), and an HRP-conjugated anti-mouse immunoglobulin antibody (Sigma). The signal was detected using chemiluminescence reagents (Pharmacia).

Figure 8:
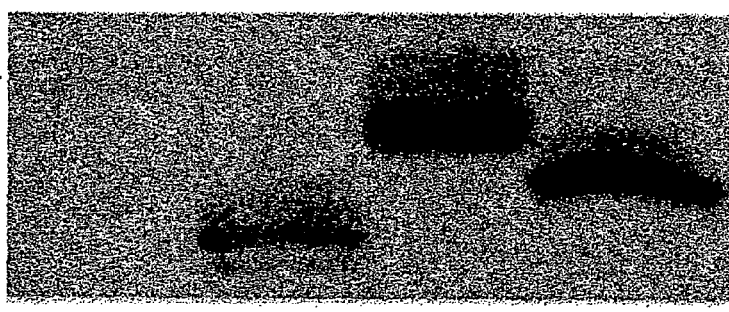
FIG. 8 is an electrophoresis photograph showing that MC-PIR2 forms a complex with ITAM-comprising signaling molecules DAP10, DAP12, and FcRγ.

In the lane containing the lysate of cells transfected with MC-PIR2 and pMKIT mock vector, no band was detected with the anti-FLAG antibody. In contrast, the same anti-FLAG antibody detected a band in the lanes containing the lysates of cells transfected with MC-PIR2 and FLAG-DAP10, or FLAG-DAP12, or FLAG-FcRγ. Thus, MC-PIR2 was shown to interact with ITAM-comprising signaling molecules, DAP10 (Wu J. et al. Science 285: 730-732 (1999)), DAP12 (Lanier L. L. et al. Nature 391: 03-707(1998)), or FcRγ (Vivier E. et al. Int. Immunol. 4: 313-1323 (1992)) (FIG. 8). The result suggests that MC-PIR2 participates in the regulation of activation signal transduction.

INDUSTRIAL APPLICABILITY

The present invention provides genes encoding novel mast cell-derived membrane proteins considered to be involved in the regulation of signal transduction in mast cells. These gene products are expected to inhibit or activate the signal transduction in mast cells following antigen stimulation through the following working hypothesis based on their expression profile and their ability to bind to proteins participating in signal transduction.

Figure 9:
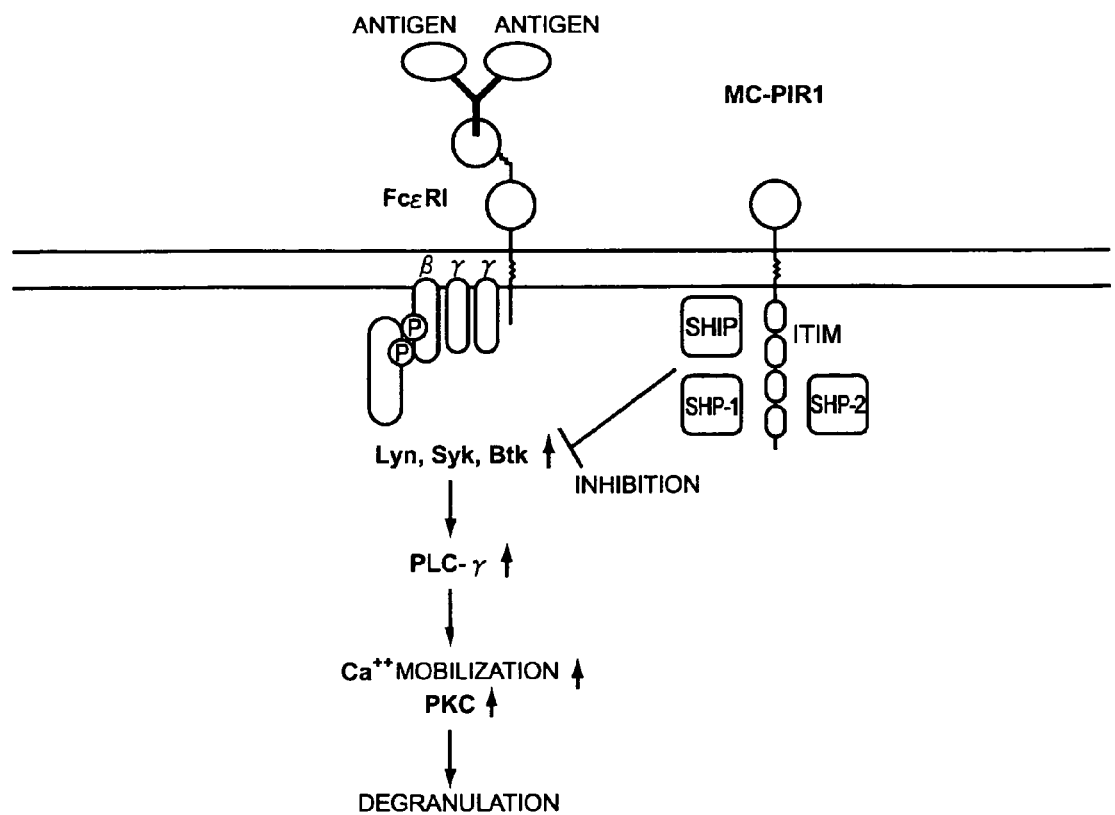
FIG. 9 schematically shows the signal transduction of FcεRI and the inhibitory function of MC-PIR1.

When FcεRI is cross-linked by IgE and antigens in mast cells, the activity of protein kinases increases in the cells, followed by increase in phosphatidylinositol turnover, which then results in an increase of intracellular calcium ion concentration and induction of degranulation. In addition, because PI3K is also activated, the level of PIP3 is increased on the plasma membrane, which leads to activation of Btk and the like (Kawakami Y. et al. Mol. Cell. Biol. 14: 5108-5113 (1994)). The inhibitory signal transduction pathways generally known are the SHIP dependent pathway (Muta T. et al. Nature 368: 70-73 (1994)) observed for FcγRIIB, and the SHP dependent pathway mediated by tyrosine phosphatases (Binstadt B. A. et al. Immunity 5: 629-638 (1996)). Because MC-PIR1 is capable of activating both pathways together, it is expected to inhibit the signaling from FcεRI more strongly (FIG. 9).

On the other hand, MC-PIR2 is capable of making a complex with ITAM-comprising signaling molecules DAP10, DAP12, and FcRγ, and thus, are expected to induce activation through kinases such as the Src family kinases, or PI3 kinase, or the like (Wu J. et al. Science 285: 730-732 (1999); Lanier L. L. et al. Nature 391: 703-707 (1998); Vivier E. et al. Int. Immunol. 4:1313-1323 (1992)). Therefore, inhibition of complex formation between MC-PIR2 and these ITAM-comprising signaling molecules is expected to inhibit the transduction of the activation signal, for example. Thus, it is possible that MC-PIR2 itself is a target molecule of suppressors of mast cell activation signal transduction.

Products of MC-PIR1 and MC-PIR2 genes, and their human homologues will be useful for screening natural ligands, compounds mimicking their effects, or antibodies. Such ligands, compounds, or antibodies obtained by the above screenings, could inhibit mast cell activation signal transduction, and can be used as anti-allergy agents that function through a novel mechanism.

The invention claimed is:

1. An isolated DNA according to any one of the following (a) to (c):
   (a) a DNA encoding a protein comprising the amino acid sequence of SEQ ID NO:2,
   (b) a DNA comprising the coding region of the nucleotide sequence of SEQ ID NO:1,
   (c) a DNA encoding a protein comprising an amino acid sequence in which up to 30 amino acids in the amino acid sequence of SEQ ID NO:2 have been replaced, deleted, inserted, and/or added, wherein the DNA encodes a protein capable of binding to a protein selected from the group consisting of SHP-1 protein, SHP-2 protein, and SHIP protein.

2. A vector into which the DNA of claim 1 has been inserted.

3. A host cell carrying the DNA of claim 1 or a vector into which the DNA of claim 1 has been inserted.

4. A method for producing a protein which comprises the steps of culturing the host cell of claim 3, and recovering the expressed protein from said host cell or the culture supernatant thereof.

5. An isolated polynucleotide comprising a segment of SEQ ID NO:1 or the complementary strand thereof, the segment being at least 15 nucleotides in length.

6. The DNA of claim 1, wherein the DNA encodes a protein comprising an amino acid sequence in which up to ten amino acids in the amino acid sequence of SEQ ID NO:2 have been replaced, deleted, inserted, and/or added.

7. The DNA of claim 1, wherein the DNA encodes a protein comprising an amino acid sequence in which up to five amino acids in the amino acid sequence of SEQ ID NO:2 have been replaced, deleted, inserted, and/or added.

8. An isolated DNA that encodes a protein that is 85% or more identical to SEQ ID NO:2, wherein the protein is capable of binding to a protein selected from the group consisting of SHP-1 protein, SHP-2 protein, and SHIP protein.

9. The DNA of claim 8, wherein the DNA encodes a protein that is 95% or more identical to SEQ ID NO:2.

10. The DNA of claim 8, wherein the DNA encodes a protein that is 96% or more identical to SEQ ID NO:2.

11. The DNA of claim 8, wherein the DNA encodes a protein that is 97% or more identical to SEQ ID NO:2.

12. The DNA of claim 8, wherein the DNA encodes a protein that is 98% or more identical to SEQ ID NO:2.

13. The DNA of claim 8, wherein the DNA encodes a protein that is 99% or more identical to SEQ ID NO:2.

14. The DNA of claim 1, wherein the DNA encodes a protein comprising the amino acid sequence of SEQ ID NO:2.

15. The DNA of claim 1, wherein the DNA comprises the coding region of the nucleotide sequence of SEQ ID NO:1.

16. The DNA of claim 1, wherein the DNA encodes a protein consisting of the amino acid sequence of SEQ ID NO:2.

17. The DNA of claim 1, wherein the DNA consists of the coding region of the nucleotide sequence of SEQ ID NO:1.

* * * * *

UNITED STATES PATENT AND TRADEMARK OFFICE
CERTIFICATE OF CORRECTION

PATENT NO. : 7,632,935 B2
APPLICATION NO. : 10/531973
DATED : December 15, 2009
INVENTOR(S) : Kitamura et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 613 days.

Signed and Sealed this

Second Day of November, 2010

David J. Kappos
*Director of the United States Patent and Trademark Office*

SEQUENCE LISTING

```
<160> NUMBER OF SEQ ID NOS: 6

<210> SEQ ID NO 1
<211> LENGTH: 1752
<212> TYPE: DNA
<213> ORGANISM: Mus musculus
<220> FEATURE:
<221> NAME/KEY: CDS
<222> LOCATION: (148)..(1104)

<400> SEQUENCE: 1
acagaactga ggaaagtcag aagcaaaaca gctagacaca aagaaaagca gaagtgggct      60
gtctcagaga ctggccgtcc cctagcggga ctgaaccgtg gagcgtccag ccgtggcctg     120
cctgccggtg acccgtgtgt gggagaa atg acc caa ctg gcc tca gct gtg tgg    174
                               Met Thr Gln Leu Ala Ser Ala Val Trp
                               1               5 ctg ccc acg ctg ttg ctg ctg ctg ctt ttt tgg ctt cca ggc tgt            222
Leu Pro Thr Leu Leu Leu Leu Leu Leu Phe Trp Leu Pro Gly Cys
10              15                  20                  25 gtc cct ctg cat ggt ccc agc acc atg aca gga agt gtg ggt caa tcc       270
Val Pro Leu His Gly Pro Ser Thr Met Thr Gly Ser Val Gly Gln Ser
                30                  35                  40 ctg agt gtg tcg tgt cag tat gag gag aaa ttt aag act aag gac aaa       318
Leu Ser Val Ser Cys Gln Tyr Glu Glu Lys Phe Lys Thr Lys Asp Lys
        45                  50                  55
```

```
tac tgg tgc aga ggg tca ctt aag gta ctg tgc aaa gat att gtc aag      366
Tyr Trp Cys Arg Gly Ser Leu Lys Val Leu Cys Lys Asp Ile Val Lys
         60                  65                  70 acc agc agc tca gaa gaa gct agg agt ggc aga gtg acc atc agg gac      414
Thr Ser Ser Ser Glu Glu Ala Arg Ser Gly Arg Val Thr Ile Arg Asp
 75                  80                  85 cat cca gac aac ctc acc ttc aca gtg acc tat gag agc ctc acc ctg      462
His Pro Asp Asn Leu Thr Phe Thr Val Thr Tyr Glu Ser Leu Thr Leu
 90                  95                 100                 105 gat gat gca gac acc tac atg tgt gcg gtg gat ata cca ttt ttc aat      510
Asp Asp Ala Asp Thr Tyr Met Cys Ala Val Asp Ile Pro Phe Phe Asn
             110                 115                 120 gcc ccc ttg ggg ctc gat aag tac ttc aag att gaa ttg tct gtg gtt      558
Ala Pro Leu Gly Leu Asp Lys Tyr Phe Lys Ile Glu Leu Ser Val Val
             125                 130                 135 cca agt gag gac cca gtt tca tct cca gga cca aca cta gag aca cct      606
Pro Ser Glu Asp Pro Val Ser Ser Pro Gly Pro Thr Leu Glu Thr Pro
             140                 145                 150 gtg gtg tcc acc agt ctg cct acc aag ggt ccc gcc cta gga tcc aac      654
Val Val Ser Thr Ser Leu Pro Thr Lys Gly Pro Ala Leu Gly Ser Asn
         155                 160                 165 aca gag gac cgc gtg gag cat gac tat tcc cag ggc ttg agg ctc cca      702
Thr Glu Asp Arg Arg Glu His Asp Tyr Ser Gln Gly Leu Arg Leu Pro
170                 175                 180                 185 gcg ctg ttg tct gtg tta gct ctc ctg ctg ttt ctg ttg gtg ggg aca      750
Ala Leu Leu Ser Val Leu Ala Leu Leu Leu Phe Leu Leu Val Gly Thr
                 190                 195                 200 tct ctg ctg gcc tgg agg atg ttc cag aag cgg ctg gtc aaa gct gat      798
Ser Leu Leu Ala Trp Arg Met Phe Gln Lys Arg Leu Val Lys Ala Asp
             205                 210                 215 agg cat cca gag ctg tcc cag aac ctc aga cag gct tct gag cag aat      846
Arg His Pro Glu Leu Ser Gln Asn Leu Arg Gln Ala Ser Glu Gln Asn
             220                 225                 230 gag tgc cag tat gtg aat ttg cag ctg cac acg tgg tct ctg agg gaa      894
Glu Cys Gln Tyr Val Asn Leu Gln Leu His Thr Trp Ser Leu Arg Glu
         235                 240                 245 gag ccg gtg cta cca agt cag gta gaa gtg gtg gaa tat agc aca ttg      942
Glu Pro Val Leu Pro Ser Gln Val Glu Val Val Glu Tyr Ser Thr Leu
250                 255                 260                 265 gca tta ccc cag gaa gag ctt cac tat tca tcc gtg gca ttc aac tcc      990
Ala Leu Pro Gln Glu Glu Leu His Tyr Ser Ser Val Ala Phe Asn Ser
                 270                 275                 280 cag agg cag gat tct cac gcc aat gga gat tct ctt cat caa cct cag     1038
Gln Arg Gln Asp Ser His Ala Asn Gly Asp Ser Leu His Gln Pro Gln
             285                 290                 295 gac cag aaa gca gag tac agt gag atc cag aag ccc aga aaa gga ctc     1086
Asp Gln Lys Ala Glu Tyr Ser Glu Ile Gln Lys Pro Arg Lys Gly Leu
         300                 305                 310 tct gac ctt tac ctg tga ctccttgtca cctgatcctc tcagtggtga            1134
Ser Asp Leu Tyr Leu
             315 ctaccaggtt ccaaggctcc ctgctggctg ctgccctcaa tgtcatgagc ctcagtggct   1194 tcactaaaga tgagcaggag ccagggctct gtgggcacag tctcatccca ctggctctct   1254 cctcttagcc tgtattttgt tctgcctctg ggtgtggaag acatcgatgc tgctcttttg   1314 gggctctggg aattgacatg gttcgtatag aacggtactt gtgttagtta gctttgtagt   1374 gtcagtccag gaagaacatc tgtggtcact gggaaagtgg gggacccatg agactacaaa   1434
```

```
ggaaggggag tcatggaggt actaaacacc aactccttca tctcacagag aaaaaaacct    1494
aagctctgag gacaaaagcc tggcccgtgg caccaaggtc aggggcaaat tcctctggac    1554 tcattttat ttttattttt tgttttttga gacagggtct ctctgtgtag ctttggctgt    1614
cctggaactc actctgtaaa ccagaatggc ctcagactca caaagatctg cctgcctctg    1674
cctccaaagg tgtgtgccac aatgcctggc ttctctgaat tcttaagtaa agatgaaat    1734 aaagtttata atatcttt                                                  1752

<210> SEQ ID NO 2
<211> LENGTH: 318
<212> TYPE: PRT
<213> ORGANISM: Mus musculus

<400> SEQUENCE: 2

Met Thr Gln Leu Ala Ser Ala Val Trp Leu Pro Thr Leu Leu Leu Leu
1               5                   10                  15

Leu Leu Leu Phe Trp Leu Pro Gly Cys Val Pro Leu His Gly Pro Ser
                20                  25                  30

Thr Met Thr Gly Ser Val Gly Gln Ser Leu Ser Val Ser Cys Gln Tyr
            35                  40                  45

Glu Glu Lys Phe Lys Thr Lys Asp Lys Tyr Trp Cys Arg Gly Ser Leu
        50                  55                  60

Lys Val Leu Cys Lys Asp Ile Val Lys Thr Ser Ser Glu Glu Ala
65                  70                  75                  80

Arg Ser Gly Arg Val Thr Ile Arg Asp His Pro Asp Asn Leu Thr Phe
                85                  90                  95

Thr Val Thr Tyr Glu Ser Leu Thr Leu Asp Asp Ala Asp Thr Tyr Met
            100                 105                 110

Cys Ala Val Asp Ile Pro Phe Phe Asn Ala Pro Leu Gly Leu Asp Lys
        115                 120                 125

Tyr Phe Lys Ile Glu Leu Ser Val Val Pro Ser Glu Asp Pro Val Ser
    130                 135                 140

Ser Pro Gly Pro Thr Leu Glu Thr Pro Val Val Ser Thr Ser Leu Pro
145                 150                 155                 160

Thr Lys Gly Pro Ala Leu Gly Ser Asn Thr Glu Asp Arg Arg Glu His
                165                 170                 175

Asp Tyr Ser Gln Gly Leu Arg Leu Pro Ala Leu Leu Ser Val Leu Ala
            180                 185                 190

Leu Leu Leu Phe Leu Leu Val Gly Thr Ser Leu Leu Ala Trp Arg Met
        195                 200                 205

Phe Gln Lys Arg Leu Val Lys Ala Asp Arg His Pro Glu Leu Ser Gln
    210                 215                 220

Asn Leu Arg Gln Ala Ser Glu Gln Asn Glu Cys Gln Tyr Val Asn Leu
225                 230                 235                 240

Gln Leu His Thr Trp Ser Leu Arg Glu Glu Pro Val Leu Pro Ser Gln
                245                 250                 255

Val Glu Val Val Glu Tyr Ser Thr Leu Ala Leu Pro Gln Glu Glu Leu
            260                 265                 270

His Tyr Ser Ser Val Ala Phe Asn Ser Gln Arg Gln Asp Ser His Ala
        275                 280                 285

Asn Gly Asp Ser Leu His Gln Pro Gln Asp Gln Lys Ala Glu Tyr Ser
    290                 295                 300

Glu Ile Gln Lys Pro Arg Lys Gly Leu Ser Asp Leu Tyr Leu
305                 310                 315
```

<210> SEQ ID NO 3
<211> LENGTH: 687
<212> TYPE: DNA
<213> ORGANISM: Mus musculus
<220> FEATURE:
<221> NAME/KEY: CDS
<222> LOCATION: (1)..(687)

<400> SEQUENCE: 3

```
atg att ccc aga gta ata aga ttg tgg ctg cct tca gct ctg ttc ctc      48
Met Ile Pro Arg Val Ile Arg Leu Trp Leu Pro Ser Ala Leu Phe Leu
1               5                   10                  15 tct cag gtc cca ggc tgt gtc cca ctg cat ggc ccc agc act atc aca      96
Ser Gln Val Pro Gly Cys Val Pro Leu His Gly Pro Ser Thr Ile Thr
            20                  25                  30 ggc gct gtt ggg gaa tcg ctc agt gtg tca tgt caa tac gag gag aaa     144
Gly Ala Val Gly Glu Ser Leu Ser Val Ser Cys Gln Tyr Glu Glu Lys
        35                  40                  45 ttc aag act aag gac aaa ttc tgg tgc aga ggg tca ctg aag gta ctc     192
Phe Lys Thr Lys Asp Lys Phe Trp Cys Arg Gly Ser Leu Lys Val Leu
    50                  55                  60 tgt aaa gat att gtc aag acc agc agc tca gaa gaa gtt agg aat ggc     240
Cys Lys Asp Ile Val Lys Thr Ser Ser Ser Glu Glu Val Arg Asn Gly
65                  70                  75                  80 cga gtg acc atc agg gac cat cca gac aac ctc acc ttc aca gtg acc     288
Arg Val Thr Ile Arg Asp His Pro Asp Asn Leu Thr Phe Thr Val Thr
                85                  90                  95 tat gag agc ctc acc ctg gag gat gca gac acc tac atg tgt gcg gtg     336
Tyr Glu Ser Leu Thr Leu Glu Asp Ala Asp Thr Tyr Met Cys Ala Val
            100                 105                 110 gat ata tca ctt ttt gat ggc tcc ttg ggg ttc gat aag tac ttc aag     384
Asp Ile Ser Leu Phe Asp Gly Ser Leu Gly Phe Asp Lys Tyr Phe Lys
        115                 120                 125 att gag ttg tct gtg gtt cca agt gag gac cca gtc aca ggt tcg agc     432
Ile Glu Leu Ser Val Val Pro Ser Glu Asp Pro Val Thr Gly Ser Ser
    130                 135                 140 ctt gag agt ggt aga gat atc ctg gaa tcc ccc aca tcc tca gtt ggg     480
Leu Glu Ser Gly Arg Asp Ile Leu Glu Ser Pro Thr Ser Ser Val Gly
145                 150                 155                 160 cac act cat ccc agt gtg acc aca gat gac aca att cct gct ccc tgc     528
His Thr His Pro Ser Val Thr Thr Asp Asp Thr Ile Pro Ala Pro Cys
                165                 170                 175 cct cag cct cgg tct ctt cgg agc agc ctc tac ttc tgg gtc ctg gtg     576
Pro Gln Pro Arg Ser Leu Arg Ser Ser Leu Tyr Phe Trp Val Leu Val
            180                 185                 190 tct ctg aag ttg ttc ctg ttc ctg agc atg ctt ggt gct gtc ctc tgg     624
Ser Leu Lys Leu Phe Leu Phe Leu Ser Met Leu Gly Ala Val Leu Trp
        195                 200                 205 gtg aac agg cct cag agg tgc tct ggg gga agc agc act cag ccc tgt     672
Val Asn Arg Pro Gln Arg Cys Ser Gly Gly Ser Ser Thr Gln Pro Cys
    210                 215                 220 tat gag aac cag tga                                                  687
Tyr Glu Asn Gln
225
```

<210> SEQ ID NO 4
<211> LENGTH: 228
<212> TYPE: PRT
<213> ORGANISM: Mus musculus

<400> SEQUENCE: 4

```
Met Ile Pro Arg Val Ile Arg Leu Trp Leu Pro Ser Ala Leu Phe Leu
 1               5                  10                  15

Ser Gln Val Pro Gly Cys Val Pro Leu His Gly Pro Ser Thr Ile Thr
            20                  25                  30

Gly Ala Val Gly Glu Ser Leu Ser Val Ser Cys Gln Tyr Glu Glu Lys
        35                  40                  45

Phe Lys Thr Lys Asp Lys Phe Trp Cys Arg Gly Ser Leu Lys Val Leu
    50                  55                  60

Cys Lys Asp Ile Val Lys Thr Ser Ser Glu Glu Val Arg Asn Gly
65                  70                  75                  80

Arg Val Thr Ile Arg Asp His Pro Asp Asn Leu Thr Phe Thr Val Thr
                85                  90                  95

Tyr Glu Ser Leu Thr Leu Glu Asp Ala Asp Thr Tyr Met Cys Ala Val
            100                 105                 110

Asp Ile Ser Leu Phe Asp Gly Ser Leu Gly Phe Asp Lys Tyr Phe Lys
        115                 120                 125

Ile Glu Leu Ser Val Val Pro Ser Glu Asp Pro Val Thr Gly Ser Ser
    130                 135                 140

Leu Glu Ser Gly Arg Asp Ile Leu Glu Ser Pro Thr Ser Ser Val Gly
145                 150                 155                 160

His Thr His Pro Ser Val Thr Thr Asp Asp Thr Ile Pro Ala Pro Cys
                165                 170                 175

Pro Gln Pro Arg Ser Leu Arg Ser Ser Leu Tyr Phe Trp Val Leu Val
            180                 185                 190

Ser Leu Lys Leu Phe Leu Phe Leu Ser Met Leu Gly Ala Val Leu Trp
        195                 200                 205

Val Asn Arg Pro Gln Arg Cys Ser Gly Gly Ser Ser Thr Gln Pro Cys
    210                 215                 220

Tyr Glu Asn Gln
225

<210> SEQ ID NO 5
<211> LENGTH: 19
<212> TYPE: DNA
<213> ORGANISM: Artificial
<220> FEATURE:
<223> OTHER INFORMATION: Artificially Synthesized Primer Sequence

<400> SEQUENCE: 5
gggggtggac catcctcta                                           19

<210> SEQ ID NO 6
<211> LENGTH: 20
<212> TYPE: DNA
<213> ORGANISM: Artificial
<220> FEATURE:
<223> OTHER INFORMATION: Artificially Synthesized Primer Sequence

<400> SEQUENCE: 6
cgcgcagctg taaacggtag                                          20
```